US006171589B1

(12) United States Patent
Browning et al.

(10) Patent No.: US 6,171,589 B1
(45) Date of Patent: Jan. 9, 2001

(54) MYCOPLASMA RECOMBINANT POLYPEPTIDES AND VACCINES

(75) Inventors: Glenn Francis Browning; Michael Francis Duffy; Kevin George Whithear; Ian Douglas Walker, all of Parkville (AU)

(73) Assignee: The University of Melbourne, Parkville (AU)

(*) Notice: Under 35 U.S.C. 154(b), the term of this patent shall be extended for 0 days.

(21) Appl. No.: 09/091,117

(22) PCT Filed: Dec. 13, 1996

(86) PCT No.: PCT/AU96/00803

§ 371 Date: Sep. 2, 1998

§ 102(e) Date: Sep. 2, 1998

(87) PCT Pub. No.: WO97/21727

PCT Pub. Date: Jun. 19, 1997

(30) Foreign Application Priority Data

Dec. 13, 1995 (AU) ........................................ PN 7127

(51) Int. Cl.$^{7}$ ......................... A61K 39/06; A61K 39/38; A61K 39/02; A61K 38/00; C07K 1/00

(52) U.S. Cl. .................................. 424/184.1; 424/184.1; 424/190.1; 530/300; 530/350; 530/387.1

(58) Field of Search ............................ 424/184.1, 190.1; 530/350, 300, 387.1

(56) References Cited

PUBLICATIONS

Lin Juey–Shin, An antigenic analysis for membranes of *Mycoplasma hominis* by cross absorption. Journal of General Microbiology, 116, 187–193, 1980.*

Liepmann et al, Use of the *Mycoplasma hominis* 102–116 kD proteins as antigen in an enzyme–linked immunosorbent assay. Microbios, 65(262) 7–13, 1991.*

Krause, DC and Robinson, DT, Mycoplasmas Molecular Biology and Pathogenesis, Mycoplasmas which infect humans, Chapter 25, pp. 417–444, 1992.*

Fraser, C.M. et al., "The minimal Gene Complement of *Mycoplasma genitalium*," (1995) *Science* 270:397–403.

Himmelreich, R. et al., "Complete sequence analysis of the genome of the bacterium *Mycpolasma pneumonia*," (1996) *Nucleic Acids Research* 24(22): 4420–4449.

* cited by examiner

*Primary Examiner*—Nita Minnifield
*Assistant Examiner*—Padma Baskar
(74) *Attorney, Agent, or Firm*—Greenlee Winner and Sullivan PC

(57) ABSTRACT

The present invention relates generally to immunogens and their use in vaccine preparations. More particularly, the present invention is directed to a peptide or polypeptide or a derivative, homologue or analogue thereof which corresponds to, mimics, or cross-reacts with, B-cell or T-cell epitopes on surface polypeptides encoded by *Mycoplasma pneumoniae* or *M. genitalium*. The immunogens of the present invention are particularly useful in vaccine preparations for the prophylactic and therapeutic treatment of individuals against infections by Mycoplasma ssp. The present invention further provides diagnostic reagents for the detection of Mycoplasma ssp. in biological samples derived from individuals suspected of being infected therewith.

28 Claims, 7 Drawing Sheets

SEQUENCE LISTING

```
(1) GENERAL INFORMATION:

   (iii) NUMBER OF SEQUENCES: 5


(2) INFORMATION FOR SEQ ID NO:1:

     (i) SEQUENCE CHARACTERISTICS:
          (A) LENGTH: 135 amino acids
          (B) TYPE: amino acid
          (D) TOPOLOGY: linear

    (ii) MOLECULE TYPE: protein

    (xi) SEQUENCE DESCRIPTION: SEQ ID NO:1:

Met Arg Lys Leu Ile Lys Leu Asn Val Ile Val Phe Val Leu Leu Tyr
  1               5                  10                  15

Leu Gly Glu Leu Phe Ala Ser Leu Ser Phe Lys Leu Ile Ser Cys Leu
             20                  25                  30

Lys Thr Arg Asn Gln Tyr Ser Leu Asn Gly Tyr Tyr Ala Leu Phe Val
         35                  40                  45

Phe Val Asn Ile Ile Gln Lys Met Ala Asn Ser Phe Gln Lys Leu Ala
     50                  55                  60

Ser Ser Val Val Leu Phe Glu Thr Glu Ile Asn Glu Phe Leu Val Leu
 65                  70                  75                  80

Phe Thr Asp Thr Lys Asn Lys Arg Glu Glu Ser Glu Pro Val Arg Gln
                 85                  90                  95
```

-continued

```
Val Ser Thr Thr Gln Glu Tyr His Gln Val Thr Leu Asp Gln Gln His
            100                 105                 110

Tyr Phe Asn His Lys Leu Ser Asp Tyr Phe Arg Leu Phe Lys Asp Lys
        115                 120                 125

Thr Phe Phe Phe Glu Ile Ile
    130                 135
```

(2) INFORMATION FOR SEQ ID NO:2:

(i) SEQUENCE CHARACTERISTICS:
(A) LENGTH: 1030 amino acids
(B) TYPE: amino acid
(D) TOPOLOGY: linear (ii) MOLECULE TYPE: protein (xi) SEQUENCE DESCRIPTION: SEQ ID NO:2:

```
Met Lys Leu Ser Ala Ile Ile Ser Leu Ser Val Ala Gly Thr Val Gly
  1               5                  10                  15

Thr Thr Ala Val Val Val Pro Thr Thr Ile Thr Leu Val Asn Lys Thr
             20                  25                  30

His Gln Val Glu His Glu Ser Glu Gln Ser Asp Phe Gln Asp Ile Arg
         35                  40                  45

Phe Gly Leu Asn Ser Val Lys Leu Pro Lys Ala Gln Pro Ala Ala Ala
     50                  55                  60

Thr Arg Ile Thr Val Glu Asn Gly Thr Asp Lys Leu Val Asn Tyr Lys
 65                  70                  75                  80

Ser Ser Pro Gln Gln Leu Phe Leu Ala Lys Asn Ala Leu Lys Asp Lys
                 85                  90                  95

Leu Gln Gly Glu Phe Asp Lys Phe Leu Ser Asp Ala Lys Ala Phe Pro
            100                 105                 110

Ala Leu Thr Ala Asp Leu Gln Glu Trp Val Asp Gln Gln Leu Phe Asn
        115                 120                 125

Pro Asn Gln Ser Phe Phe Asp Leu Ser Ala Pro Arg Ser Asn Phe Thr
    130                 135                 140

Leu Ser Ser Asp Lys Lys Ala Ser Leu Asp Phe Ile Phe Arg Phe Thr
145                 150                 155                 160

Asn Phe Thr Glu Ser Val Gln Leu Leu Lys Leu Pro Glu Gly Val Ser
                165                 170                 175

Val Val Val Asp Ser Lys Gln Ser Phe Asp Tyr Tyr Val Asn Ala Ser
            180                 185                 190

Ala Gln Lys Leu Leu Val Leu Pro Leu Ser Leu Pro Asp Tyr Thr Leu
        195                 200                 205

Gly Leu Asn Tyr Met Phe Asp His Ile Thr Leu Asn Gly Lys Val Val
    210                 215                 220

Asn Lys Phe Ser Phe Asn Pro Phe Lys Thr Asn Leu Asn Leu Ala Phe
225                 230                 235                 240

Ser Asn Val Tyr Asn Gly Val Asp Val Phe Glu Ala Gln Lys Asn Leu
                245                 250                 255

Val Gly Lys Gly Lys Tyr Leu Asn Thr His Val Lys Ala Glu Asp Val
            260                 265                 270

Lys Lys Asp Val Asn Ala Asn Ile Lys Asn Gln Phe Asp Ile Ala Lys
        275                 280                 285

Ile Ile Ala Glu Leu Met Gly Lys Ala Leu Lys Glu Phe Gly Asn Gln
    290                 295                 300
```

-continued

```
Gln Glu Gly Gln Pro Leu Ser Phe Leu Lys Val Met Asp Lys Val Lys
305                 310                 315                 320

Glu Asp Phe Glu Lys Leu Phe Asn Leu Val Arg Pro Gly Leu Gly Lys
                325                 330                 335

Phe Val Lys Gly Leu Ile Gln Ser Ser Ser Gln Ala Glu Asn Lys Ile
            340                 345                 350

Thr Val Tyr Lys Leu Ile Phe Asp Asn Lys Lys Thr Ile Leu Asn Leu
        355                 360                 365

Leu Lys Glu Leu Ser Ile Pro Glu Leu Asn Ser Ser Leu Gly Leu Val
    370                 375                 380

Asp Val Leu Phe Asp Val Ile Thr Asp Ser Asp Gly Leu Tyr Glu Arg
385                 390                 395                 400

Leu Gln Ser Phe Lys Asp Leu Ile Val Pro Ala Val Lys Thr Asn Glu
                405                 410                 415

Lys Thr Ala Ala Leu Ser Pro Leu Ile Glu Glu Leu Leu Thr Gln Lys
            420                 425                 430

Asp Thr Tyr Val Phe Asp Leu Ile Gln Lys His Lys Gly Ile Leu Thr
        435                 440                 445

Asn Leu Leu Lys Asn Phe Leu Ala Asp Phe Gln Lys Ser Thr Pro Phe
    450                 455                 460

Met Ala Asp Gln Val Ala Ile Phe Thr Glu Leu Phe Asp Asn Glu Gly
465                 470                 475                 480

Ala Phe Asp Leu Phe Gly Glu Ala Asp Phe Val Asp Lys Ile Ala Glu
                485                 490                 495

Leu Phe Leu Thr Lys Arg Thr Val Lys Asn Gly Glu Lys Ile Glu Thr
            500                 505                 510

Lys Asp Ser Leu Leu Val Thr Ser Leu Lys Ser Leu Leu Gly Glu Lys
        515                 520                 525

Val Ala Ala Leu Asp Asp Leu Leu Asp Ser Tyr Ile Phe Lys Asn Glu
    530                 535                 540

Leu Leu Asn Arg Ser Val Glu Val Ala Lys Ala Glu Ala Lys Asp Thr
545                 550                 555                 560

Lys Gly Ala Thr Asp Tyr Lys Lys Glu Gln Ala Lys Ala Leu Lys Lys
                565                 570                 575

Leu Phe Lys His Ile Gly Glu Asn Thr Leu Ser Lys Thr Asn Leu Asp
            580                 585                 590

Lys Ile Thr Leu Lys Glu Val Lys Asn Thr Glu Asn Val Glu Leu Glu
        595                 600                 605

Glu Thr Glu Thr Thr Leu Lys Val Lys Lys Leu Asp Val Glu Tyr Lys
    610                 615                 620

Val Glu Leu Gly Asn Phe Glu Ile Lys Asn Gly Leu Ile Lys Ala Met
625                 630                 635                 640

Leu Glu Phe Leu Pro Asp Pro Lys Asp Leu Glu Thr Thr Leu Asp Lys
                645                 650                 655

Leu Leu Phe Lys Gly Glu Ser Tyr Lys Ala Met Lys Asp Lys Tyr Ile
            660                 665                 670

Lys Glu Gly Phe Pro Gly Tyr Gly Trp Ala Lys Gly Val Val Pro Gly
        675                 680                 685

Ala Phe Glu Ser Ile Glu Asn Thr Phe Lys Ser Ala Ile Asp Lys Thr
    690                 695                 700

Lys Ser Ile Arg Asp Leu Phe Gly Asp Met Leu Phe Gly Asn Asp Leu
705                 710                 715                 720

Ser Ser Val Lys Glu Thr Asp Ser Phe Ile Thr Leu Gly Gly Ser Phe
```

-continued

```
            725                 730                 735

Asp Ile Lys Tyr Gly Gly Glu Asn Leu Asn Val Leu Pro Ala Tyr Tyr
        740                 745                 750

Ser Leu Ile Asn Ser Glu Ile Gly Tyr Gln Ile Ile Gly Val Asp Thr
    755                 760                 765

Thr Ile Asp Ala Thr Lys Val Lys Val Glu Leu Lys Asn Lys Glu Tyr
    770                 775                 780

Lys Gly Lys Ser Pro Ala Ile Asn Gly Gln Val Lys Leu Ser Gln Ser
785                 790                 795                 800

Phe Phe Asn Val Trp Thr Asn Met Phe Asp Ser Ile Thr Lys Gln Ile
            805                 810                 815

Phe Gln Lys Lys Tyr Glu Phe Lys Asp Asn Ile Gln Val Phe Ala Arg
        820                 825                 830

Asn Glu Asp Asn Thr Ser Arg Leu Glu Leu Asp Ile Ser Asp Pro Glu
    835                 840                 845

Gln Arg Val Ile Pro Phe Ala Phe Val Asp Gly Phe Gly Ile Gln Leu
    850                 855                 860

Lys Ala Val Asp Lys Asn Ile Thr Lys Glu Ala Gly Asn Thr Glu Pro
865                 870                 875                 880

Lys Ser Pro Val Ile Gln Leu Tyr Glu Ala Leu Asn Lys Glu Lys Asp
            885                 890                 895

Gln Lys Gln Gln Ser Lys Gln Ser Pro Lys Gln Leu Asp Thr Lys Thr
        900                 905                 910

Gln Leu Gly Tyr Leu Leu Lys Leu Gly Asp Asn Trp Ser Lys Asp Asp
    915                 920                 925

Tyr Lys Ser Leu Ile Asp Asp Thr Ile Ile Asn Asn Asn Tyr Leu Glu
    930                 935                 940

Ala Ser Phe Asn Ser Lys Ile Thr Val Asp Arg Leu Gly Ile Pro Ile
945                 950                 955                 960

Asp Leu Trp Leu Phe Lys Ile Trp Pro Lys Phe Asn Leu Glu Ile Pro
            965                 970                 975

Met Gln Gly Ser Leu Gln Leu Tyr Ser Ser Ser Val Ile Phe Pro Tyr
        980                 985                 990

Gly Ile Tyr Asp Thr Ser Val Gln Asp Ala Thr Lys Ile Val Lys Arg
    995                 1000                1005

Leu Asn Phe Thr Asp Met Gly Phe Lys Leu Asn Asp Pro Lys Pro Asn
    1010                1015                1020

Phe Trp Phe Val Gly Phe
1025                1030
```

(2) INFORMATION FOR SEQ ID NO:3:

(i) SEQUENCE CHARACTERISTICS:
(A) LENGTH: 4071 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(A) ORGANISM: Mycoplasma pneumoniae (ix) FEATURE:
(A) NAME/KEY: CDS
(B) LOCATION: 250..654

(ix) FEATURE:
(A) NAME/KEY: CDS

-continued (B) LOCATION: 762..3851
(D) OTHER INFORMATION: /codon= (seq: "tga" 3648..3651,
aa: Trp)
/codon=(seq: "tga" 3663..3665, aa:Trp)

(xi) SEQUENCE DESCRIPTION: SEQ ID NO:3:

```
GCACCATCCA AATGGCTTAC AACGAACAAC ACCACAAAAC ACCAATGACG GTGCAAAAAC     60

CAATTACCTT AAACCAGCCG TTAAGTTAAA GACCAAAAGC TCAGAGCAGC AAAAAGCTGC    120

TTTAATTAAG CAGCTAACCA AGGAAATGAA GCAAGCAGCC GCTAACCAAA ACTATGAGTT    180

AGCGATTGAG ATCCGCGACT CGATCTTTGA ATTGGAAAAG CAATTTCGTG GTAAAATTAA    240

GAGCTAGCA ATG CGT AAA CTA ATT AAA TTA AAC GTC ATT GTC TTT GTC        288
          Met Arg Lys Leu Ile Lys Leu Asn Val Ile Val Phe Val
            1               5                  10

TTG TTG TAC TTG GGC GAG CTG TTT GCC AGC CTT TCG TTC AAG TTA ATC      336
Leu Leu Tyr Leu Gly Glu Leu Phe Ala Ser Leu Ser Phe Lys Leu Ile
     15                  20                  25

AGT TGC CTC AAG ACA CGC AAC CAG TAC TCC TTA AAC GGG TAC TAT GCG      384
Ser Cys Leu Lys Thr Arg Asn Gln Tyr Ser Leu Asn Gly Tyr Tyr Ala
 30                  35                  40                  45

TTG TTT GTC TTT GTC AAC ATC ATC CAA AAG ATG GCT AAC TCT TTC CAA      432
Leu Phe Val Phe Val Asn Ile Ile Gln Lys Met Ala Asn Ser Phe Gln
                 50                  55                  60

AAG TTA GCT TCC TCA GTT GTG TTG TTT GAA ACT GAA ATT AAC GAA TTT      480
Lys Leu Ala Ser Ser Val Val Leu Phe Glu Thr Glu Ile Asn Glu Phe
             65                  70                  75

TTA GTT CTC TTT ACT GAT ACA AAG AAT AAG CGT GAG GAG AGT GAA CCA      528
Leu Val Leu Phe Thr Asp Thr Lys Asn Lys Arg Glu Glu Ser Glu Pro
         80                  85                  90

GTG CGC CAG GTG TCA ACA ACC CAA GAG TAT CAC CAG GTT ACG CTC GAC      576
Val Arg Gln Val Ser Thr Thr Gln Glu Tyr His Gln Val Thr Leu Asp
     95                 100                 105

CAA CAA CAC TAC TTT AAC CAC AAA CTG AGC GAT TAC TTC CGT TTG TTT      624
Gln Gln His Tyr Phe Asn His Lys Leu Ser Asp Tyr Phe Arg Leu Phe
110                 115                 120                 125

AAG GAC AAA ACT TTC TTC TTT GAA ATT ATC TAGTTACTAA ATTGACCTGA        674
Lys Asp Lys Thr Phe Phe Phe Glu Ile Ile
                130                 135

ATTGCAACCT TTCAGGCACT TTTTACTGTT AGTAACTAGT CTTTTTTCAT TTCAATATTT    734

AAGTTTTTAA TTTAACCAAT TTTTACT ATG AAG CTT AGT GCT ATT ATC TCC        785
                              Met Lys Leu Ser Ala Ile Ile Ser
                                1               5

CTA TCA GTC GCT GGT ACT GTG GGA ACA ACT GCG GTG GTA GTA CCT ACA      833
Leu Ser Val Ala Gly Thr Val Gly Thr Thr Ala Val Val Val Pro Thr
     10                  15                  20

ACT ATA ACG CTT GTA AAT AAG ACC CAC CAA GTA GAA CAT GAA TCA GAA      881
Thr Ile Thr Leu Val Asn Lys Thr His Gln Val Glu His Glu Ser Glu
 25                  30                  35                  40

CAA TCG GAT TTT CAA GAT ATT CGC TTT GGT CTT AAT AGT GTT AAG TTG      929
Gln Ser Asp Phe Gln Asp Ile Arg Phe Gly Leu Asn Ser Val Lys Leu
                 45                  50                  55

CCA AAA GCA CAG CCA GCT GCG GCA ACT AGA ATT ACC GTG GAA AAC GGG      977
Pro Lys Ala Gln Pro Ala Ala Ala Thr Arg Ile Thr Val Glu Asn Gly
             60                  65                  70

ACT GAT AAA TTA GTC AAC TAT AAG TCC TCA CCA CAA CAA CTC TTT TTA     1025
Thr Asp Lys Leu Val Asn Tyr Lys Ser Ser Pro Gln Gln Leu Phe Leu
         75                  80                  85

GCG AAG AAC GCG CTT AAG GAT AAA CTC CAA GGT GAG TTT GAT AAA TTC     1073
Ala Lys Asn Ala Leu Lys Asp Lys Leu Gln Gly Glu Phe Asp Lys Phe
```

-continued

```
    90                  95                  100

CTA AGT GAT GCG AAG GCC TTC CCA GCG CTA ACC GCT GAT TTA CAG GAA     1121
Leu Ser Asp Ala Lys Ala Phe Pro Ala Leu Thr Ala Asp Leu Gln Glu
105                 110                 115                 120

TGG GTT GAC CAA CAG CTG TTT AAT CCA AAC CAA AGT TTC TTT GAT TTA     1169
Trp Val Asp Gln Gln Leu Phe Asn Pro Asn Gln Ser Phe Phe Asp Leu
                125                 130                 135

AGT GCG CCC AGG TCA AAC TTT ACC CTT TCA TCT GAC AAA AAG GCT AGT     1217
Ser Ala Pro Arg Ser Asn Phe Thr Leu Ser Ser Asp Lys Lys Ala Ser
            140                 145                 150

TTA GAC TTT ATC TTC CGC TTT ACT AAC TTC ACC GAA TCC GTT CAG TTG     1265
Leu Asp Phe Ile Phe Arg Phe Thr Asn Phe Thr Glu Ser Val Gln Leu
        155                 160                 165

TTA AAA CTA CCA GAA GGT GTA TCG GTT GTA GTT GAC TCC AAA CAA AGC     1313
Leu Lys Leu Pro Glu Gly Val Ser Val Val Val Asp Ser Lys Gln Ser
    170                 175                 180

TTT GAT TAC TAT GTC AAT GCT AGT GCC CAA AAA TTA TTA GTT CTA CCG     1361
Phe Asp Tyr Tyr Val Asn Ala Ser Ala Gln Lys Leu Leu Val Leu Pro
185                 190                 195                 200

CTG TCT TTA CCA GAT TAC ACT TTG GGT TTA AAC TAT ATG TTT GAC CAC     1409
Leu Ser Leu Pro Asp Tyr Thr Leu Gly Leu Asn Tyr Met Phe Asp His
                205                 210                 215

ATT ACT TTA AAC GGT AAG GTT GTC AAT AAA TTT AGT TTT AAT CCG TTC     1457
Ile Thr Leu Asn Gly Lys Val Val Asn Lys Phe Ser Phe Asn Pro Phe
            220                 225                 230

AAA ACG AAT TTA AAC CTC GCC TTT AGC AAC GTT TAC AAT GGC GTT GAT     1505
Lys Thr Asn Leu Asn Leu Ala Phe Ser Asn Val Tyr Asn Gly Val Asp
        235                 240                 245

GTG TTT GAA GCA CAA AAG AAT TTA GTA GGT AAG GGT AAA TAC CTC AAC     1553
Val Phe Glu Ala Gln Lys Asn Leu Val Gly Lys Gly Lys Tyr Leu Asn
    250                 255                 260

ACC CAC GTG AAG GCT GAA GAC GTA AAG AAG GAC GTT AAT GCC AAC ATT     1601
Thr His Val Lys Ala Glu Asp Val Lys Lys Asp Val Asn Ala Asn Ile
265                 270                 275                 280

AAA AAC CAA TTT GAC ATT GCC AAA ATT ATC GCT GAG CTA ATG GGT AAA     1649
Lys Asn Gln Phe Asp Ile Ala Lys Ile Ile Ala Glu Leu Met Gly Lys
                285                 290                 295

GCC CTT AAA GAA TTT GGC AAT CAA CAA GAA GGT CAA CCA TTA TCC TTC     1697
Ala Leu Lys Glu Phe Gly Asn Gln Gln Glu Gly Gln Pro Leu Ser Phe
            300                 305                 310

CTA AAG GTA ATG GAT AAA GTT AAA GAA GAT TTT GAA AAA CTG TTT AAC     1745
Leu Lys Val Met Asp Lys Val Lys Glu Asp Phe Glu Lys Leu Phe Asn
        315                 320                 325

TTA GTC CGT CCT GGA TTG GGT AAA TTT GTT AAG GGC TTA ATC CAA AGT     1793
Leu Val Arg Pro Gly Leu Gly Lys Phe Val Lys Gly Leu Ile Gln Ser
    330                 335                 340

AGT AGT CAA GCA GAA AAC AAG ATA ACT GTC TAC AAG TTA ATC TTT GAC     1841
Ser Ser Gln Ala Glu Asn Lys Ile Thr Val Tyr Lys Leu Ile Phe Asp
345                 350                 355                 360

AAC AAA AAG ACC ATC TTA AAC CTA CTT AAA GAG CTT TCC ATT CCG GAA     1889
Asn Lys Lys Thr Ile Leu Asn Leu Leu Lys Glu Leu Ser Ile Pro Glu
                365                 370                 375

TTA AAC TCT TCT TTA GGT TTA GTG GAC GTC TTG TTT GAT GTC ATT ACT     1937
Leu Asn Ser Ser Leu Gly Leu Val Asp Val Leu Phe Asp Val Ile Thr
            380                 385                 390

GAC TCT GAT GGT CTC TAT GAA AGG TTG CAA TCT TTC AAA GAC TTA ATC     1985
Asp Ser Asp Gly Leu Tyr Glu Arg Leu Gln Ser Phe Lys Asp Leu Ile
        395                 400                 405

GTT CCA GCA GTT AAA ACG AAT GAA AAA ACC GCG GCT TTA AGT CCA TTA     2033
```

-continued

```
Val Pro Ala Val Lys Thr Asn Glu Lys Thr Ala Ala Leu Ser Pro Leu
    410                 415                 420

ATT GAA GAG TTA TTA ACC CAA AAG GAT ACC TAT GTG TTT GAC TTA ATT      2081
Ile Glu Glu Leu Leu Thr Gln Lys Asp Thr Tyr Val Phe Asp Leu Ile
425                 430                 435                 440

CAA AAA CAC AAG GGT ATC TTG ACT AAC TTG TTA AAG AAC TTC TTA GCT      2129
Gln Lys His Lys Gly Ile Leu Thr Asn Leu Leu Lys Asn Phe Leu Ala
                445                 450                 455

GAT TTC CAA AAA TCA ACG CCG TTT ATG GCT GAT CAA GTA GCC ATC TTC      2177
Asp Phe Gln Lys Ser Thr Pro Phe Met Ala Asp Gln Val Ala Ile Phe
            460                 465                 470

ACT GAG TTA TTT GAC AAC GAA GGT GCG TTT GAT TTA TTT GGT GAG GCT      2225
Thr Glu Leu Phe Asp Asn Glu Gly Ala Phe Asp Leu Phe Gly Glu Ala
        475                 480                 485

GAC TTT GTT GAC AAG ATT GCC GAA CTC TTC TTA ACA AAG CGT ACT GTT      2273
Asp Phe Val Asp Lys Ile Ala Glu Leu Phe Leu Thr Lys Arg Thr Val
    490                 495                 500

AAA AAT GGT GAA AAA ATT GAA ACT AAA GAT TCC CTA CTG GTA ACA TCA      2321
Lys Asn Gly Glu Lys Ile Glu Thr Lys Asp Ser Leu Leu Val Thr Ser
505                 510                 515                 520

TTA AAG AGT CTT TTA GGG GAA AAG GTA GCT GCC TTA GAT GAT TTG TTA      2369
Leu Lys Ser Leu Leu Gly Glu Lys Val Ala Ala Leu Asp Asp Leu Leu
                525                 530                 535

GAT AGC TAC ATC TTT AAA AAT GAA TTA CTT AAC CGC AGT GTA GAA GTG      2417
Asp Ser Tyr Ile Phe Lys Asn Glu Leu Leu Asn Arg Ser Val Glu Val
            540                 545                 550

GCT AAG GCT GAA GCT AAG GAC ACT AAA GGT GCT ACC GAT TAC AAA AAG      2465
Ala Lys Ala Glu Ala Lys Asp Thr Lys Gly Ala Thr Asp Tyr Lys Lys
        555                 560                 565

GAA CAA GCT AAG GCG CTC AAA AAA CTC TTT AAA CAC ATT GGT GAA AAC      2513
Glu Gln Ala Lys Ala Leu Lys Lys Leu Phe Lys His Ile Gly Glu Asn
    570                 575                 580

ACT TTA AGT AAA ACC AAT CTC GAT AAA ATC ACC TTA AAA GAA GTT AAA      2561
Thr Leu Ser Lys Thr Asn Leu Asp Lys Ile Thr Leu Lys Glu Val Lys
585                 590                 595                 600

AAC ACC GAA AAT GTT GAA TTA GAA GAA ACT GAA ACA ACC TTA AAG GTT      2609
Asn Thr Glu Asn Val Glu Leu Glu Glu Thr Glu Thr Thr Leu Lys Val
                605                 610                 615

AAA AAA CTC GAT GTT GAA TAC AAG GTA GAA CTT GGC AAC TTT GAA ATC      2657
Lys Lys Leu Asp Val Glu Tyr Lys Val Glu Leu Gly Asn Phe Glu Ile
            620                 625                 630

AAG AAT GGC TTG ATT AAG GCA ATG CTC GAA TTC TTG CCA GAC CCT AAA      2705
Lys Asn Gly Leu Ile Lys Ala Met Leu Glu Phe Leu Pro Asp Pro Lys
        635                 640                 645

GAT TTA GAA ACA ACT TTA GAT AAA CTC TTG TTC AAA GGG GAA AGC TAC      2753
Asp Leu Glu Thr Thr Leu Asp Lys Leu Leu Phe Lys Gly Glu Ser Tyr
    650                 655                 660

AAA GCG ATG AAA GAC AAG TAC ATC AAG GAA GGT TTC CCT GGT TAT GGT      2801
Lys Ala Met Lys Asp Lys Tyr Ile Lys Glu Gly Phe Pro Gly Tyr Gly
665                 670                 675                 680

TGG GCT AAA GGA GTA GTC CCT GGG GCC TTT GAA TCT ATT GAA AAT ACT      2849
Trp Ala Lys Gly Val Val Pro Gly Ala Phe Glu Ser Ile Glu Asn Thr
                685                 690                 695

TTT AAG AGT GCT ATT GAT AAA ACC AAG TCC ATT CGT GAT CTC TTT GGC      2897
Phe Lys Ser Ala Ile Asp Lys Thr Lys Ser Ile Arg Asp Leu Phe Gly
            700                 705                 710

GAC ATG CTC TTT GGT AAC GAT TTA AGC AGC GTT AAA GAA ACT GAT TCA      2945
Asp Met Leu Phe Gly Asn Asp Leu Ser Ser Val Lys Glu Thr Asp Ser
        715                 720                 725
```

-continued

```
TTC ATC ACC CTA GGT GGT TCG TTC GAC ATT AAG TAT GGC GGT GAA AAT      2993
Phe Ile Thr Leu Gly Gly Ser Phe Asp Ile Lys Tyr Gly Gly Glu Asn
    730                 735                 740

CTC AAT GTG TTG CCA GCT TAC TAC TCT TTA ATT AAC AGC GAA ATT GGC      3041
Leu Asn Val Leu Pro Ala Tyr Tyr Ser Leu Ile Asn Ser Glu Ile Gly
745                 750                 755                 760

TAT CAA ATT ATT GGT GTA GAT ACC ACA ATT GAT GCA ACT AAG GTA AAA      3089
Tyr Gln Ile Ile Gly Val Asp Thr Thr Ile Asp Ala Thr Lys Val Lys
                765                 770                 775

GTT GAA TTA AAA AAC AAA GAG TAT AAG GGT AAA TCG CCA GCT ATT AAC      3137
Val Glu Leu Lys Asn Lys Glu Tyr Lys Gly Lys Ser Pro Ala Ile Asn
            780                 785                 790

GGT CAG GTG AAG TTG TCA CAA TCA TTC TTT AAT GTT TGG ACA AAT ATG      3185
Gly Gln Val Lys Leu Ser Gln Ser Phe Phe Asn Val Trp Thr Asn Met
        795                 800                 805

TTT GAC AGC ATT ACC AAA CAA ATC TTC CAA AAG AAA TAC GAG TTC AAA      3233
Phe Asp Ser Ile Thr Lys Gln Ile Phe Gln Lys Lys Tyr Glu Phe Lys
    810                 815                 820

GAT AAC ATC CAA GTG TTT GCG CGA AAC GAA GAT AAC ACA TCA CGT TTA      3281
Asp Asn Ile Gln Val Phe Ala Arg Asn Glu Asp Asn Thr Ser Arg Leu
825                 830                 835                 840

GAA CTT GAC ATT TCT GAT CCT GAA CAA CGG GTA ATT CCA TTT GCT TTT      3329
Glu Leu Asp Ile Ser Asp Pro Glu Gln Arg Val Ile Pro Phe Ala Phe
                845                 850                 855

GTT GAT GGC TTT GGC ATT CAA CTC AAA GCA GTT GAC AAA AAC ATT ACG      3377
Val Asp Gly Phe Gly Ile Gln Leu Lys Ala Val Asp Lys Asn Ile Thr
            860                 865                 870

AAA GAA GCA GGT AAT ACT GAG CCA AAA TCT CCT GTA ATT CAA CTT TAT      3425
Lys Glu Ala Gly Asn Thr Glu Pro Lys Ser Pro Val Ile Gln Leu Tyr
        875                 880                 885

GAG GCA CTT AAT AAA GAA AAA GAT CAA AAA CAA CAA AGT AAA CAA TCT      3473
Glu Ala Leu Asn Lys Glu Lys Asp Gln Lys Gln Gln Ser Lys Gln Ser
    890                 895                 900

CCA AAA CAA CTT GAT ACT AAA ACA CAG TTG GGT TAC CTA TTG AAA TTA      3521
Pro Lys Gln Leu Asp Thr Lys Thr Gln Leu Gly Tyr Leu Leu Lys Leu
905                 910                 915                 920

GGC GAC AAT TGG AGT AAA GAT GAT TAC AAA AGC TTA ATT GAT GAT ACG      3569
Gly Asp Asn Trp Ser Lys Asp Asp Tyr Lys Ser Leu Ile Asp Asp Thr
                925                 930                 935

ATC ATC AAT AAC AAC TAT TTA GAG GCC AGC TTT AAT TCC AAG ATA ACG      3617
Ile Ile Asn Asn Asn Tyr Leu Glu Ala Ser Phe Asn Ser Lys Ile Thr
            940                 945                 950

GTT GAT CGC TTG GGT ATT CCT ATT GAC CTT TGA TTG TTT AAG ATT TGA      3665
Val Asp Arg Leu Gly Ile Pro Ile Asp Leu Trp Leu Phe Lys Ile Trp
        955                 960                 965

CCT AAG TTC AAT TTG GAA ATC CCA ATG CAA GGT TCC TTA CAA CTT TAC      3713
Pro Lys Phe Asn Leu Glu Ile Pro Met Gln Gly Ser Leu Gln Leu Tyr
    970                 975                 980

AGT AGT AGT GTT ATC TTC CCA TAC GGT ATT TAT GAC ACC AGT GTT CAA      3761
Ser Ser Ser Val Ile Phe Pro Tyr Gly Ile Tyr Asp Thr Ser Val Gln
985                 990                 995                 1000

GAT GCT ACG AAG ATT GTG AAG CGT CTG AAC TTT ACT GAC ATG GGC TTC      3809
Asp Ala Thr Lys Ile Val Lys Arg Leu Asn Phe Thr Asp Met Gly Phe
                1005                1010                1015

AAA CTC AAC GAT CCA AAA CCT AAC TTC TGG TTC GTT GGT TTT              3851
Lys Leu Asn Asp Pro Lys Pro Asn Phe Trp Phe Val Gly Phe
            1020                1025                1030

TAGAGCAGAC TAACTACTAT ACTGATTAAG CTACCTAGAA GGTAAAGGCG AGAAGTTCAT    3911

CCACCAAAAC CCGCGGGTTG TTTACGGTAG GATGAACTTT TTGCTTTATA CTCGTCAAAA    3971
```

-continued

CTAATGTTGG GCTTGGCGTA TATCTACCTA GTTTTAGATA TTGGTTAAAC TTGCTAATTT 4031

CGTACCGTGC TCCATCACAG GTCTTTAAGC GCACTATACC 4071

(2) INFORMATION FOR SEQ ID NO:4:

(i) SEQUENCE CHARACTERISTICS:
(A) LENGTH: 137 amino acids
(B) TYPE: amino acid
(D) TOPOLOGY: linear (ii) MOLECULE TYPE: protein (vi) ORIGINAL SOURCE:
(A) ORGANISM: Mycoplasma genitalium (xi) SEQUENCE DESCRIPTION: SEQ ID NO:4:

```
Met Arg Gln Phe Ile Lys Leu Ser Leu Leu Val Phe Val Leu Leu Phe
1               5                   10                  15

Leu Ser Glu Leu Ile Cys Arg Phe Ser Leu Arg Leu Val Asn Ser Ile
            20                  25                  30

Lys Ala Arg Tyr Lys Ser Ser Val Phe Ser Tyr Thr Ala Cys Leu Leu
        35                  40                  45

Phe Leu Lys Ser Phe Gln Asn Phe Ser Asn Ala Phe Gln Lys Leu Ala
    50                  55                  60

Asn Trp Val Phe Trp Phe Glu Asn Asp Val Asn Glu Leu Leu Ser Ile
65                  70                  75                  80

Phe Tyr Phe Asn Phe Asp Gln Lys Ser Glu Lys Val Asp Tyr Asn Phe
                85                  90                  95

Phe Asn Gly Tyr Lys Val Thr Ala Gln Lys Val Val Glu Lys Glu Gln
            100                 105                 110

Leu Leu Thr Cys Lys Leu Ser Asp Tyr Tyr Arg Leu Phe Arg Asp Lys
        115                 120                 125

Thr Phe Trp Phe Glu Leu Ile Asn Asn
    130                 135
```

(2) INFORMATION FOR SEQ ID NO:5:

(i) SEQUENCE CHARACTERISTICS:
(A) LENGTH: 1024 amino acids
(B) TYPE: amino acid
(D) TOPOLOGY: linear (ii) MOLECULE TYPE: protein (vi) ORIGINAL SOURCE:
(A) ORGANISM: Mycoplasma genitalium (xi) SEQUENCE DESCRIPTION: SEQ ID NO:5:

```
Met Lys Leu Ser Thr Ile Thr Thr Ile Cys Leu Ser Ile Ser Gly Ala
1               5                   10                  15

Phe Gly Thr Thr Ala Ile Ala Leu Pro Thr Thr Val Ala Leu Leu Lys
            20                  25                  30

Asn His Gln Gln Gln Asn Thr Glu Lys Gln Gln Asn Pro Ile Lys Asp
        35                  40                  45

Ile Arg Phe Gly Leu Asn Asn Val Gln Val Pro Asn Thr Ile Pro Leu
    50                  55                  60

His Gln Thr Val Val Glu Val Thr Asn Asn Lys Ala Ile Val Asp Tyr
65                  70                  75                  80

Lys Asp Ala Pro Gln Lys Phe Phe Leu Ala Lys Ser Ala Leu Asn Asn
                85                  90                  95
```

-continued

```
Lys Leu Gln Val Glu Phe Asp Lys Phe Leu Leu Arg Thr Gly Val Ile
            100                 105                 110

Asn Ala Leu Asn Ala Asp Leu Lys Glu Trp Ile Asp Gln Thr Leu Phe
        115                 120                 125

Ile Pro Asn Gln Ser Phe Phe Asp Leu Ser Ala Asn Lys Leu Asn Leu
    130                 135                 140

Thr Leu Ser Asn Gln Ser Glu Val Ser Leu Asp Leu Glu Phe Ile Phe
145                 150                 155                 160

Thr Asn Phe Ser Asp Lys Asn Gln Pro Leu Lys Leu Pro Phe Asp Gly
                165                 170                 175

Ser Val Val Val Asn Ala Asn Glu Ser Tyr Thr Tyr Ser Val Lys Ala
            180                 185                 190

Thr Leu Gln Lys Leu Lys Val Leu Thr Tyr Ser Arg Ala Asp His Ser
        195                 200                 205

Val Gly Ile Ser Tyr Ala Ile Pro Thr Val Ser Leu Asn Gly Lys Thr
    210                 215                 220

Gln Asn Asp Phe Ser Phe Asn Pro Phe Lys Ser Asn Ile Asn Phe Ala
225                 230                 235                 240

Phe Lys Asn Val Tyr Asn Ala Leu Asn Pro Phe Glu Ala Gln Gln Tyr
                245                 250                 255

Leu Val Gly Gln Gly Lys Phe Leu Asn Gln Lys Val Asn Ala Asp Asp
            260                 265                 270

Val Lys Asn Asp Ile Asn Asn His Ile Glu Thr Gln Phe Asn Val Ala
        275                 280                 285

Lys Ile Thr Ala Thr Leu Leu Gly Lys Ala Phe Lys Gln Phe Gly Glu
    290                 295                 300

His Lys Asn Gly Gln Pro Leu Ser Leu Leu Lys Val Leu Ser Gly Leu
305                 310                 315                 320

Asn Asn Glu Phe Lys Gln Leu Phe Asn Tyr Val Arg Pro Gly Leu Gly
                325                 330                 335

Asp Phe Val Ser Asp Leu Ile Gln Ser Ser Ser Gln Ser Ser Asn Lys
            340                 345                 350

Lys Thr Val Tyr Gln Leu Leu Phe Glu Asn Lys Thr Thr Ile Ile His
        355                 360                 365

Leu Leu Gln Asp Leu Asn Ile Ser Glu Leu Asn Ser Val Leu Pro Val
    370                 375                 380

Val Asp Ile Leu Phe Glu Gly Ile Asn Ser Ala Glu Ser Leu Tyr Gln
385                 390                 395                 400

Arg Ile Gln Ser Phe Lys Asp Leu Ile Val Pro Ala Leu Lys Ala Asp
                405                 410                 415

Lys Gln Leu Lys Ser Leu Glu Ala Ile Ile Leu Ala Val Leu Asp Asn
            420                 425                 430

Pro Asn Thr Tyr Val Phe Asp Leu Val Tyr Gln Asn Lys Ser Ile Leu
        435                 440                 445

Phe Asn Leu Leu Ser Asp Phe Leu Lys Asn Thr Ala Asn Thr Leu Pro
    450                 455                 460

Phe Leu Gln Glu Gln Phe Asp Ile Val Asn His Leu Phe Ala Asn Glu
465                 470                 475                 480

Ala Ile Phe Asp Leu Phe Ser Asn Ala Asp Phe Val Glu Lys Ile Ala
                485                 490                 495

Asp Leu Phe Leu Ala Lys Gln Lys Val Gln Glu Val Asn Asn Asp Gly
            500                 505                 510
```

-continued

```
Thr Lys Ser Thr Lys Ile Val Asp Ser Ile Leu Val Ala Thr Leu Lys
        515                 520                 525

Gly Leu Val Gly Asp Gln Leu Ser Ser Ile Thr Glu Leu Leu Asn Ile
    530                 535                 540

Tyr Ile Phe Glu Asn Glu Phe Leu Asn Arg Asn Asp Ser Asn Ser Ser
545                 550                 555                 560

Val Lys Lys Gln Gln Thr Asp Ser Leu Lys Asn Leu Phe Ser Val Ile
                565                 570                 575

Gly Asp Ile Leu Ser Glu Thr Asn Val Asn Lys Ile Thr Leu His Ala
            580                 585                 590

Val Lys Asn Asn Glu Leu Leu Ser Leu Val Glu Thr Ala Ser Thr Leu
        595                 600                 605

Lys Ile Lys His Leu Asn Val Gln Tyr Lys Val Leu Val Asp Lys Phe
    610                 615                 620

Glu Leu Lys Asn Ser Phe Ile Lys Glu Leu Leu Asn Phe Phe Pro Asp
625                 630                 635                 640

Thr Lys Asp Ile Thr Pro Thr Ile Lys Lys Val Leu Phe Glu Ser Glu
                645                 650                 655

Asn Tyr Lys Thr Leu Arg Lys Lys Tyr Glu Asn Glu Gly Phe Pro Gly
            660                 665                 670

Tyr His Trp Ala Lys Phe Ile Val Pro Gly Thr Phe Asn Ser Ala Glu
        675                 680                 685

Asn Thr Phe Tyr Ser Ala Ile Asp Lys Thr Lys Ser Ile Arg Asp Leu
    690                 695                 700

Phe Ala Asp Met Leu Phe Gly Lys Ser Leu Glu Ser Val Asn Asp Ser
705                 710                 715                 720

Asp Ser Phe Ile Lys Ile Asn Gly Ser Phe Thr Leu Lys Tyr His Gly
                725                 730                 735

Asp Asn Leu Asn Leu Leu Pro Asn Tyr His Ser Leu Ile Thr Lys Asn
            740                 745                 750

Val Gly Tyr Gln Ile Val Asn Val Asn Phe His Ile Asp Ala Arg Leu
        755                 760                 765

Leu Thr Ala Glu Leu Gln Asn Thr Val Phe Ser Asn Pro Lys Pro Val
    770                 775                 780

Ile Lys Ser Pro Val Glu Leu Ser Lys Ser Leu Phe Glu Val Trp Lys
785                 790                 795                 800

Thr Ile Phe Glu Asn Ser Val Asn Gln Ile Leu Lys Lys Glu Tyr Thr
                805                 810                 815

Phe Lys Asp Asn Leu Lys Phe Phe Pro Phe Lys Ala Asp Gly Ser Ser
            820                 825                 830

Arg Leu Glu Phe Asp Leu Ser Lys Pro Asp Gln Arg Val Ile Pro Phe
        835                 840                 845

Ala Phe Val Asp Gly Tyr Gln Phe Gln Leu Lys Lys Glu Leu Ile Pro
    850                 855                 860

Asn Lys Glu Thr Lys Lys Glu Ala Asn Ser Ser Pro Val Leu Lys Leu
865                 870                 875                 880

Tyr Asp Ala Val Lys Arg Asn Asp Arg Gln Tyr Arg Pro Asn His His
                885                 890                 895

His Asp Asp Leu Arg Asn Tyr Pro Ser Leu Lys Ser Gln Leu Glu Leu
            900                 905                 910

Ile Leu Asn Leu Gly Asp Lys Leu Lys Ala Asn Asn Asp Phe Ile Asp
        915                 920                 925

Asp Thr Val Val Asn Ala Leu Gln Tyr Lys Thr Ser Phe Lys Ser Thr
```

-continued

```
    930                 935                 940

Leu Lys Val Asn Ser Leu Gly Ile Pro Ile Asn Leu Phe Phe Phe Thr
945                 950                 955                 960

Leu Trp Leu Lys Phe Asn Leu Glu Ile Pro Ile Asp Gly Ser Leu Thr
                965                 970                 975

Leu Thr Ser Val Asn Val Val Phe Pro Tyr Ser Leu Tyr Asp Thr Ser
            980                 985                 990

Ser Asn Glu Phe Thr Arg Ile Val Asp Arg Leu Asn Phe Thr Asp Thr
        995                 1000                1005

Asn Phe Tyr Leu Lys Asp Ala Phe Pro Asn Phe Trp Phe Val Gly Phe
    1010                1015                1020
```

MYCOPLASMA RECOMBINANT POLYPEPTIDES AND VACCINES

The present invention relates generally to peptides and polypeptides and their use in vaccine preparations. More particularly, the present invention is directed to a peptide or polypeptide or a derivative, homologue or analogue thereof which corresponds to, mimics, or cross-reacts with, B-cell or T-cell epitopes on polypeptides encoded by *Mycoplasma pneumoniae* and *M. genitalium*. Vaccine preparations comprising the peptides or polypeptides of the present invention are useful in protecting individuals against infections by species of the genus Mycoplasma.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

Bibliographic details of the publications referred to by author in this specification are collected at the end of the description.

Sequence identity numbers (SEQ ID Nos.) for the nucleotide and amino acid sequences referred to in the specification are defined after the bibliography.

The micro-organisms *Mycoplasma pneumoniae* is a pathogen of humans that typically colonises the upper respiratory tract. *Mycoplasma pneumoniae* moves along the cilia of the respiratory epithelium until in close association with the host cell to which it adheres. It disrupts the protein ciliary necklace at the base of the host cell cilia causing ciliostasis.

The threat the *M. pneumoniae* poses to children and sensitized adults is considerable. *Mycoplasma pneumoniae* is the primary cause of atypical pneumonia in young adults and children, although infected patients often present with symptoms similar to a persistent influenza infection. A study performed in the U.K. (Granstrom et al, 1994) has attributed 18% of the total number of cases of acquired pneumonia in the community, to *M. pneumoniae* infection. Periodically, *M. pneumoniae* is present in epidemic proportions in human communities. Previous exposure to the pathogen can result in hypersensitivity reactions upon reinfection (Cimolai et al, 1992).

Although only one in one thousand cases of *M. pneumoniae* infection result in pathology of the central nervous system (CNS), infection is associated with 5–10% of cases of neurological syndromes (Koskiniemi, 1993). Typical CNS manifestations associated with infection include encephalitis, meningitis and myelitis. Additional complications associated with *M. pneumoniae* infection include the presence of cold agglutinins and arthropathy (Cimolai et al, 1989). A report of Zagami et al. (1994) suggests that the neurological pathology of *M. pneumoniae* associated encephalitis results from a cell mediated response to shared *M. pneumoniae* antigens, or a local inflammatory response of the CNS due to the presence of *M. pneumoniae* in the CNS.

However, notwithstanding the endemic and serious nature of *M. pneumoniae* related disease, no means is available for the accurate and rapid diagnosis of *M. pneumoniae* infection, or for the prophylaxis of individuals exposed to infection. Accordingly, there is a clear need to develop agents useful in the diagnosis and prophylaxis of infection by mycoplasmas, in particular *M. pneumoniae*.

Previous attempts to develop a suitable peptide vaccine against *M. pneumoniae* have been largely unsuccessful. For example, although hamsters immunised with *M. pneumoniae* may develop antibodies against the P1 protein of *M. pneumoniae*, the results, in terms of the degree of humoral immunity conferred by such immunisation, have been inconsistent and unpredictable (Yayoshi et al, 1992). In particular, hamsters inoculated with the P24-SII live vaccine, which contains the P1 protein but not the 85 kDa protein, were not protected against infection. The P24-SI live vaccine, containing the P1 protein and the 85 kDa protein, gave 50% protection against infection. The FH-P24 live vaccine, also containing both the P1 protein and the 85 kDa protein, gave 90% protection. The P24-SI and P24-SII vaccines are nitroso guanidine non-hemolysing mutants of FH-P24. Furthermore, no success has been obtained using the 43 kDa *M. pneumoniae* protein, which appears to enhance the severity of infection by this pathogen (Cimolai et al, 1992).

In work leading up to the present invention, the inventors sought to develop better and more effective vaccines and diagnostic agents for *M. pneumoniae*, by cloning. *M. pneumoniae* genes encoding highly immunogenic polypeptides and homologues and derivatives thereof. The recombinant polypeptides and derivatives, homologues or analogues thereof, provide the means to develop a range of diagnostic and prophylactic agents for Mycoplasma infection which were hitherto not available.

Accordingly, one aspect of the present invention is directed to an isolated or recombinant polypeptide or a derivative, homologue or analogue thereof wherein said polypeptide is obtainable from a species of Mycoplasma.

In one embodiment of the present invention, there is provided an isolated or recombinant polypeptide or derivative, homologue or analogue thereof wherein said polypeptide is obtainable from a species of Mycoplasma and has a predicted molecular weight of approximately 16 kDa.

Preferably, the isolated or recombinant polypeptide of the present invention or a derivative, homologue or analogue thereof is further obtainable from *Mycoplasma pneumoniae* or *M. genitalium* and *M. genitalium.*

More preferably, said polypeptide further comprises an amino acid sequence substantially the same as the amino acid sequence set forth in SEQ ID NO:1 or SEQ ID NO:4, or is at least 70% similar to all or a part thereof.

In one particularly preferred embodiment, the isolated or recombinant polypeptide or a derivative, homologue or analogue thereof is characterised by any one or more of the following properties:

(I) it is obtainable from *Mycoplasma pneumoniae;*

(ii) it has a predicted molecular weight of approximately 16 kDa; or (iii) it comprises an amino acid sequence substantially as set forth in SEQ ID NO:1 or having at least 70% similarity to all or a part thereof.

Alternatively or in addition, the isolated or recombinant polypeptide or a derivative, homologue or analogue thereof is characterised by any one of the following properties:

(I) it is obtainable from *Mycoplasma genitalium;*

(ii) it has a predicted molecular weight of approximately 16 kDa; or (iii) it comprises an amino acid sequence substantially as set forth in SEQ ID NO:4 or having at least 70% similarity to all or a part thereof.

The homologous amino acid sequences set forth in SEQ ID Nos:1 and 4 are only 37.3% identical overall, as described in Example 21. Accordingly, the present invention further extends to any isolated Mycoplasma polypeptide which has properties of a surface polypeptide and is at least 35% identical to SEQ ID NO:1 or SEQ ID NO:4.

In an alternative embodiment of the present invention, there is provided an isolated polypeptide, or a derivative, homologue or analogue thereof wherein said polypeptide is obtainable from a species of Mycoplasma and wherein said polypeptide in its native form is a surface polypeptide which has adhesion properties.

Preferably, one embodiment is directed to an isolated polypeptide, or a derivative, homologue or analogue thereof wherein said polypeptide is obtainable from *Mycoplasma pneumoniae*, has a molecular weight of approximately 110 kDa determined by SDS/PAGE, or a predicted molecular weight of approximately 116 kDa and in its native form is a surface polypeptide which has adhesion properties.

For the present purposes, it will be understood that reference to the molecular weight of the subject polypeptide does not necessarily limit the invention, but is included especially for the purposes of nomenclature. Those skilled in the art are aware of the degree of precision associated with molecular weight estimates in respect of protein or polypeptide molecules and the fact that such estimates vary considerably depending upon the means employed to obtain them. For example, the subject polypeptide having derived molecular weight of 116 kDa may electrophorese on SDS/polyacrylamide gels such that it has an estimated molecular weight of only 110 kDa. Accordingly, reference herein to the term "116 kDa polypeptide" or "110 kDa polypeptide" are not to be taken as mutually exclusive definitions.

Even more particularly, this embodiment of the present invention is directed to an isolated polypeptide or derivative, homologue or analogue thereof characterised by the following properties:

(I) it is obtainable from *Mycoplasma pneumoniae;*

(ii) it has a molecular weight of approximately 110 kDa as determined by SDS/PAGE, or a predicted molecular weight of approximately 116 kDa;

(iii) it is a surface polypeptide in its native form;

(iv) it has adhesion properties in its native form; or (v) it comprises an amino acid sequence substantially as set forth in SEQ ID NO:2 or having at least 70% similarity to all or a part thereof.

Alternatively, this embodiment is directed to an isolated polypeptide, or a derivative, homologue or analogue thereof wherein said polypeptide is obtainable from *Mycoplasma genitalium.*

Accordingly, this alternative embodiment is directed to an isolated polypeptide or derivative, homologue or analogue thereof characterised by any of the following properties:

(I) it is obtainable from *Mycoplasma genitalium;*

(ii) it is at least 50% identical to the amino acid sequence set forth in SEQ ID NO:2;

(iii) it has the structural properties of a surface polypeptide; or (iv) it comprises an amino acid sequence substantially as set forth in SEQ ID NO:5 or having at least 70% similarity to all or a part thereof.

The present invention extends to both isolated non-recombinant polypeptides, recombinant polypeptides and isolated recombinant polypeptides of Mycoplasma described in any of the foregoing embodiments.

In particular, the present invention extends to isolated non-recombinant polypeptides, recombinant polypeptides and isolated recombinant polypeptides comprising a sequence of amino acids substantially as set fort in SEQ ID NO:1 or SEQ ID NO:2 or SEQ ID NO:4 or SEQ ID NO:5 or having at least 70% similarity to all or a part thereof.

According to the foregoing embodiments, when the polypeptide of the present invention is a recombinant polypeptide, it may be produced in and, if desirable isolated from, any virus particle or cell. As will be known to those skilled in the relevant art, a cell for production of a recombinant polypeptide is selected on the basis of several parameters including the genetic constructs used to express the polypeptide under consideration, stability and activity of said polypeptide. It will also be known to those skilled in the art, that the stability or activity of a recombinant polypeptide may be determined, at least in part, by post-translational modifications to the polypeptide, for example glycosylation, acylation or alkylation reactions, amongst others, which may vary between cell lines used to produce the recombinant polypeptide.

The present invention extends further to a recombinant polypeptide according to any of the foregoing embodiments or a derivative, homologue or analogue thereof, wherein said polypeptide is produced in any virus particle or a prokaryotic or eukaryotic cell or a culture thereof.

In a preferred embodiment, the present invention extends to a recombinant polypeptide according to any of the foregoing embodiments or a derivative, homologue or analogue thereof, wherein said polypeptide is produced in a bacterial cell or culture thereof belonging to the genus Mycoplasma, in particular a cell of *M. pneumoniae* or *M. genitalium* or a culture thereof or an *Escherichia coli* cell.

The term "polypeptide" as used herein shall be taken to refer to any polymer consisting of amino acids linked by covalent bonds and includes within its scope full-length proteins and parts or fragments thereof, for example oligopeptides and short peptide sequences consisting of at least two amino acid residues. Also included within the scope of the definition of a "polypeptide" are amino acid sequence variants, containing amino acid substitutions, deletions, or insertions which do not alter the essential properties of said polypeptide, for example its immunogenicity or effectiveness as a peptide vaccine against Mycoplasma ssp, amongst others. Accordingly, a polypeptide may be isolated from a source in nature, or chemically synthesized. Furthermore, a polypeptide may be derived from a full-length protein by chemical or enzymatic cleavage, using reagents such as CNBr, trypsin, or chymotrypsin, amongst others.

The term "recombinant polypeptide" as used herein shall be taken to refer to a polypeptide which is produced in a virus particle or a cell by the expression therein of a genetic sequence encoding said polypeptide under the control of a suitable promoter, wherein a genetic manipulation has been performed in order to achieve said expression. Genetic manipulations will be known to those skilled in the art and include, but are not limited to nucleic acid isolation, digestion, ligation, amplification, hybridisation or sequencing.

The term "surface polypeptide" or similar term as used herein shall be taken in its broadest context to refer to a polypeptide which is localised on, or intrinsically or extrinsically associated with, the surface layer of *Mycoplasma spp.* and in particular *M. pneumoniae* or *M. genitalium.* A surface polypeptide, or at least an epitope thereof, is accessible to recognition by the immune system of the host organism without lysis of the infecting pathogen.

The term "adhesion properties" as used herein shall be taken to refer to a functional characteristic of a polypeptide which facilitates the association, adherence or attachment of a micro-organism to a cell of a host organism during the infectious phase. In the present context, adhesion properties of the micro-organism usually render *M. pneumoniae* capable of binding host cells of the upper respiratory tract.

The term "native form" or "native state" or similar term as used herein with reference to a characteristic of a polypeptide, shall be taken as a reference to the inherent properties of a non-recombinant polypeptide when it is present in the cell from which it originates, such as a mycoplasma cell, in particular a *M. pneumoniae* cell. For example, the *M. pneumoniae* polypeptide set forth in SEQ ID NO:2 has a predicted molecular weight of 116 kDa and is said to be in its native state when it is in a *M. pneumoniae* cell and no genetic manipulations have been performed upon it. Accordingly, said polypeptide when present in a *M. pneumoniae* cell, has the inherent properties of being localised to the cell surface and is an adhesion polypeptide.

The term "predicted molecular weight" as used herein in relation to a polypeptide refers to a molecular weight which is determined by a summation of the molecular weights of individual chemical elements or atoms comprised therein.

In a more particularly preferred embodiment, the present invention extends to a recombinant polypeptide or a derivative, homologue or analogue thereof produced in a virus particle, prokaryotic or eukaryotic cell or a virus or cell culture thereof, wherein said recombinant polypeptide has an amino acid sequence which is substantially the same as the amino acid sequence set forth in SEQ ID NO:1 or SEQ ID NO:2 or a part thereof.

It is understood in the art that although parts or fragments of a full-length protein may not possess all of the properties of the full-length protein, they are at least useful as diagnostic reagents, or as immunogens in the production of immunoreactive molecules or vaccine preparations. Accordingly, the present invention extends to parts or fragments of an isolated polypeptide defined according to the embodiments herein.

In a particularly preferred embodiment, the present invention extends to a part or fragment of the isolated or recombinant form of a polypeptide set forth in SEQ ID NO:1 or SEQ ID NO:2

In a more particularly preferred embodiment of the invention, there is provided a fragment or derivative of the amino acid sequence of the forth in SEQ ID NO:2 comprising amino acid residues 9 to 473, 467 to 709, 709 to 850, 846 to 896, 887 to 962 or 969 to 1029 of said amino acid sequence or a homologue, analogue or derivative thereof. The specific fragments or derivatives of SEQ ID NO: 2 to which this embodiment of the invention relates are exemplified in Table 5 which is incorporated herein.

Even more particularly preferred, the fragment or derivative of SEQ ID NO:2 is highly immunogenic or antigenic, preferably when compared to the full-length amino acid sequence. Those skilled in the art will be aware that such peptide derivatives or fragments are useful as immunogens which comprise a B cell or T cell epitope. Particularly suitable for this purpose is a fragment or derivative of SEQ ID NO: 2 comprising amino acid residues 9 to 473 of SEQ ID NO: 2 or a homologue, analogue or derivative thereof.

The polypeptide, or a derivative, homologue or analogue thereof of the present invention is particularly useful as a polypeptide component in a vaccine composition which is designed to protect an individual against infection by a species of Mycoplasma, in particular to protect an individual against infection by *Mycoplasma pneumoniae* or *M. genitalium*. The essential feature of said polypeptide, or derivative, homologue or analogue thereof for the present purpose is whether it is "immunogenic", defined hereinafter as the ability of said polypeptide, or a derivative, homologue or analogue thereof, to elicit B cell and/or T cell responses in the host, as part of the immunization process. It is understood by a person skilled in the art that not all parts of a polypeptide or derivative, homologue or analogue thereof are equally immunogenic. In fact, a polypeptide or a derivative, homologue or analogue thereof may be comprised of several different overlapping, or non-overlapping regions, which, in isolation, or in combination, are highly immunogenic. Said highly immunogenic region, or a derivative, homologue or analogue thereof, is hereinafter referred to as a "B cell and/or T cell epitope".

Furthermore, a B cell or T cell epitope of a polypeptide or a derivative, homologue or analogue thereof may comprise any one or more of the following:

(I) the primary amino acid sequence of said region, known in the art as a continuous non-conformational epitope;

(ii) the secondary structure which said region adopts, known in the art as a continuous conformational epitope;

(iii) the tertiary structure which said region adopts in contact with another region of the same polypeptide molecule, known in the art as a discontinuous conformational epitope; or (iv) the quaternary structure which said region adopts in contact with a region of another polypeptide molecule, known in the art as a discontinuous conformational epitope.

Accordingly, immunogenic polypeptides or derivatives, homologues or analogues thereof comprising the same, or substantially the same primary amino acid sequence are hereinafter defined as "immunogens which comprise a B cell or T cell epitope", or similar term.

Immunogenic polypeptides or derivatives, homologues, or analogues thereof comprising different primary amino acid sequences may comprise immunologically identical immunogens, because they possess conformational B cell or T cell epitopes that are recognised by the immune system of a host species to be identical. Such immunogenic polypeptides or derivatives, homologues or analogues thereof are hereinafter defined as "immunogens which mimic or cross-react with a B cell or T cell epitope", or similar term.

Accordingly, the present invention extends to an immunogen which comprsies, mimics, or cross-reacts with a B-cell or T-cell epitope of an isolated or recombinant polypeptide according to any of the foregoing embodiments or a derivative, homologue or analogue thereof. In a particularly preferred embodiment, the present invention provides an immunogen which comprises, mimics, or cross-reacts with a B-cell or T-cell epitope of an isolated or recombinant polypeptide which in its native form is obtainable from a species of Mycoplasma such as, but not limited to *M. pneumoniae* and has a predicted molecular weight of approximately 16 kDa or a homologue, analogue or derivative thereof. According to this embodiment, when the polypeptide has a predicted molecular weight of approximately 116 kDa it is also preferred that said polypeptide in its native form is a surface polypeptide with adhesion properties.

In a particularly preferred embodiment of the invention, there is provided an immunogen comprising amino acid resides 9 to 473, 467 to 709, 709 to 850, 846 to 896, 887 to 962 or 969 to 1029 of SEQ ID NO: 2 or a homologue, analogue or derivative thereof. More particularly, the preferred immunogen, according to this embodiment of the invention, comprises amino acid residues 9 to 473 of SEQ ID NO: 2 or a homologue, analogue or derivative thereof.

In an alternative embodiment, the present invention extends to an immunogen which comprises, mimics, or cross-reacts with a B-cell or T-cell epitope of a polypeptide according to any of the foregoing embodiments or a derivative, homologue or analogue thereof, wherein said polypeptide comprises a sequence of amino acids which is at least about 40% similar to the amino acid sequence set forth in SEQ ID NO:1 or SEQ ID NO:2, more preferably at least about 60% similar, still more preferably at least about 80% similar and even still more preferably, at least about 99% similar to the amino acid sequence set forth in SEQ ID NO:1 or SEQ ID NO:2.

In the present context, "homologues" of a polypeptide refer to those polypeptides, enzymes or proteins which have similar properties as a polypeptide of the present invention, for example surface protein adhesion properties or immunogenic properties as described supra, notwithstanding any amino acid substitutions, additions or deletions thereto.

Furthermore, amino acids may be replaced by other amino acids having similar properties, for example hydrophobicity, hydrophilicity, hydrophobic moment, antigenicity, propensity to form a break α-helical structures or β-sheet structures, and so on.

The present invention clearly extends to such amino acid variants, provided that such molecules still function as B cell or T-cell epitopes capable of mediating an immune response or functioning as a surface polypeptide. Preferably, a homologue will still function as a peptide immunogen which mimics or cross-reacts to B-cell or T-cell epitopes of a *Mycoplasma spp.* polypeptide of the present invention.

Furthermore, a homologue may be isolated or derived from the same or another Mycoplasma species. Preferred sources of homologues of a *Mycoplasma pneumoniae* polypeptide according to the present invention are *M. genitalium, M. penetrans, M. iowae, M. gallisepticum, M. imitans, M. muris, M. urealyticum* or *M. pirum*, amongst others. In a particularly preferred embodiment of the invention, homologues of the *M. pneumoniae* 16 kDa and 116 kDa polypeptide are isolated from *M. genitalium*. The amino acid sequence of the *M. genitalium* homologue of the 16 kDa polypeptide is set forth in SEQ ID NO:4. The amino acid sequence of the *M. genitalium* homologue of the 116 kDa polypeptide is set forth in SEQ ID NO:5.

Substitutions encompass amino acid alterations in which an amino acid is replaced with a different naturally-occurring or a non-conventional amino acid residue. Such substitutions may be classified as "conservative", in which case an amino acid residue contained in a repressor polypeptide is replaced with another naturally-occurring amino acid of similar character, for example Gly↔Ala, Val↔Ile↔Leu, Asp↔Glu, Lys↔Arg, Asn↔Gln or Phe↔Trp↔Tyr.

Substitutions encompassed by the present invention may also be "non-conservative", in which an amino acid residue is substituted with an amino acid having different properties, such as a naturally-occurring amino acid from a different group (eg. substituted a charged or hydrophobic amino acid with alanine), or alternatively, in which a naturally-occurring amino acid is substituted with a non-conventional amino acid.

Amino acid substitutions are typically of single residues, but may be clustered depending upon functional constraints placed upon the polypeptide; insertions will usually be of the order of about 1–10 amino acid residues; and deletions will range from about 1–20 residues. Amino acid alterations to the peptides contemplated herein include insertions such as amino acid and/or carboxyl terminal fusions as well as intra-sequence insertions of single or multiple amino acids. Generally, insertions within the amino acid sequence will be smaller than amino or carboxyl terminal fusions, of the order of about 1 to 4 residues. Insertional amino acid sequence variants are those in which one or more amino acid residues are introduced into a predetermined site in the protein. Deletional variants are characterised by the removal of one or more amino acids from the sequence. Substitutional variants are those in which at least one residue in the sequence has been removed and a different residue inserted in its place. Such substitutions may be made in accordance with Table 1.

The amino acid variants referred to in Table 1 may readily be made using peptide synthetic techniques well known in the art, such as solid phase peptide synthesis and the like, or by recombinant DNA manipulations. Techniques for making substitution mutations at predetermined sites in DNA having known sequence are well known, for example through M13 mutagenesis. The manipulation of DNA sequences to produce variant proteins which manifest as substitutional, insertional or deletional variants are well known in the art.

TABLE 1

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

"Analogues" encompass polypeptides which are functionally equivalent or at least have similar properties as a polypeptide of the present invention, notwithstanding the occurrence of any non-naturally occurring or modified amino acid residues therein. Non-naturally occurring amino acid residues contemplated in an analogue of the present invention are set forth in Table 2.

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methyl-asparagine | Nmasn |
| | | L-N-methylaspartic acid | Nmasp |
| aminoisobutyric acid | Aib | L-N-methylcysteine | Nmcys |
| aminonorbornyl-carboxylate | Norb | L-N-methylgluta-mine | Nmgln |
| | | L-N-methylglutamic acid | Nmglu |
| cyclohexylalanine | Chexa | L-N-methylhistidine | Nmhis |
| cyclopentylalanine | Cpen | L-N-methylisol-leucine | Nmile |
| D-alanine | Dal | L-N-methylleucine | Nmleu |
| D-arginine | Darg | L-N-methyllysine | Nmlys |

TABLE 2-continued

| Non-conventional amino acid | Code | Non-conventional amino acid | Code |
|---|---|---|---|
| D-aspartic acid | Dasp | L-N-methylmethionine | Nmmet |
| D-cysteine | Dcys | LN-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalaline | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-amino-isobutyrate | Maib |
| D-valine | Dval | α-methyl-γ-amino-butyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-phenylethyl) glycine | Nbhm |
| D-N-methylcysteine | Dnmcys | N-(3,3-diphenylpropyl) glycine | Nbhe |
| D-N-methylglutamine | Dnmgln | N-(3-guanidinopropyl) glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl)) glycine | Nhis |
| D-N-methylleucine | Dnmleu | N-(3-indolylyethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methylanapthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl) glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomo phenylalanine | Nmhphe |
| N-(N-(2,2-diphenylethyl) carbamylmethyl)glycine | Nnbhm | N-(N-3,3-diphenylpropyl) carbamylmethyl)glycine | Nnbhe |
| 1-carboxy-1-(2,2-diphenylethylamino)cyclopropane | Nmbc | | |

The term "derivative" in relation to a polypeptide as hereinbefore defined shall be taken to refer hereinafter to mutants, parts or fragments of a functional molecule. Derivatives also include modified peptides in which ligands are attached to one or more of the amino acid residues contained therein, such as carbohydrates, enzymes, proteins, polypeptides or reporter molecules such as radionuclides or fluorescent compounds. Glycosylated, fluorescent, acylated or alkylated forms of the subject polypeptides are particularly contemplated by the present invention. Additionally, derivatives of a polypeptide as hereinbefore defined may comprise fragments or parts of an amino acid sequence disclosed herein and are within the scope of the invention, as are homopolymers or heteropolymers comprising two or more copies of the subject polypeptides. Procedures for derivatizing peptides are well-known in the art.

Particularly preferred derivatives of a polypeptide according to the present invention include amino acid residues 9 to

473, 467 to 709, 709 to 850, 846 to 896, 887 to 962 or 969 to 1029 of the amino acid sequence set forth in SEQ ID NO:2. These derivative polypeptides are exemplified in Table 5 herein.

In a most particularly preferred embodiment of the invention, the derivative is useful as an immunogen to elicit the production of antibodies capable of recognising *Mycoplasma pneumoniae* or at least a protein component thereof. According to this embodiment, there is provided a recombinant polypeptide derivative of SEQ ID NO:2 comprising amino acids 9 to 473 thereof.

The present invention extends further to derivatives, homologues or analogues of the derivative polypeptide provided herein, which are at least useful as immunogens.

Other examples of recombinant or synthetic mutants and derivatives of the peptide immunogens of the present invention include single or multiple substitutions, deletions and/or additions to any molecule associated with the ligand such as carbohydrates, lipids and/or proteins or polypeptides. Naturally occurring or altered glycosylated or acylated forms of the subject peptides are particularly contemplated by the present invention. Additionally, homopolymers or heteropolymers comprising one or more copies of the subject peptide listed in SEQ ID NO:1 or SEQ ID NO:2, or one or more derivatives, homologues or analogues thereof, are within the scope of the invention.

The immunogen of the present invention as described supra or a derivative, homologue or analogue thereof is useful in vaccine compositions and/or as an antigen to elicit polyclonal and monoclonal antibody production and/or in the detection of antibodies against *M. pneumoniae* in infected individuals.

To improve the immunogenicity of a subject polypeptide of the present invention one or more amino acids not corresponding to the original protein sequence may be added to the amino or carboxyl terminus of the polypeptide. Such extra amino acids are useful for coupling the polypeptides to another peptide or polypeptide, to a large carrier protein or to a solid support. Amino acids that are useful for these purposes include but are not limited to tyrosine, lysine, glutamic acid, aspartic acid, cysteine and derivatives thereof. Additional protein modification techniques may be used, e.g., $NH_2$-acetylation or COOH-terminal amidation, to provide additional means for coupling the polypeptides to another polypeptide, protein, or peptide molecular, or a support. Procedures for coupling polypeptides to each other, carrier proteins and solid supports are well known in the art. Furthermore, the polypeptide may be immobilised to a polymeric carrier or support material which possesses immunogenic properties. Polypeptides containing the abovementioned extra amino acid residues at either the carboxyl- or amino- termini and either uncoupled or coupled to a carrier or solid support, are consequently within the scope of the present invention.

In an alternative embodiment, the immunogenicity of a polypeptide immunogen may be improved using molecular biology techniques to produce a fusion protein containing one or more of the polypeptide of the present invention and a highly immunogenic protein. For example, fusion proteins containing a polypeptide which is of low immunogenicity and the highly immunogenic B subunit of cholera toxin may induce an immune response to the polypeptide. The present invention also contemplates the use of genes encoding cytokines, for example interleukin, in fusion with the subject polypeptide immunogen.

Preferably, the polypeptide immunogen or a derivative, homologue or analogue thereof when administered to a mammal mediates an immune response in said mammal. More preferably, the immunogen of the present invention when administered to a mammal, induces humoral immunity against *Mycoplasma spp.* in particular *M. pneumoniae* or *M. genitalium* in said primate. Still more preferably, the immunogen when administered, prevents the onset, development or progression, of symptoms associated with *Mycoplasma pneumoniae* infections, for example atypical pneumonia, or lung lesions, or inflammation of the respiratory tract, or inflammation of the central nervous system, amongst others.

The invention further encompasses functionally equivalent variants, derivatives, homologues or analogues of the amino acid sequence set forth in SEQ ID NO:1 or SEQ ID NO:2, which do not significantly reduce the immunogenic and/or antigenic properties of said polypeptide. Such functionally equivalent derivatives and homologues are as described supra. The invention also encompasses homopolymers or heteropolymers of one or more of the polypeptides set forth in SEQ ID NO:1 or SEQ ID NO:2, and derivatives, homologues or analogues thereof are within the scope of the invention. Also within the scope of this invention are polypeptides of fewer amino acid residues than the subject polypeptides but which encompass one or more immunogenic epitopes present in any one of the polypeptides and thus retain the immunogenic and/or antigenic properties of the base polypeptide.

The use of polypeptide analogues can result in polypeptides with increased immunogenic and/or antigenic activity, that are less sensitive to enzymatic degradation, and which are more selective. A suitable proline analogue is 2-aminocyclopentane carboxylic acid ($\beta Ac^5c$) which has been shown to increase the immunogenic activity of a native polypeptide more than 20 times (Mierke et al., 1990; Portoghese et al., 1990; Goodman et al., 1987).

In a related embodiment, the present invention provides a substantially homogeneous form of any one or more polypeptide immunogens selected from the list comprising SEQ ID NO:1 and SEQ ID NO:2 or a derivative, homologue or analogue thereof, wherein the term "substantially homogeneous" is defined herein as being in a form suitable for interaction with an immunologically interactive molecule. Preferably, the immunogen is at least 20% homogeneous, more preferably at least 75% homogeneous and yet still more preferably at least about 95–100% homogeneous, in terms of percentage purity on a weight-for-weight basis.

Accordingly, the present invention extends to a method of purifying an polypeptide immunogen of the present invention, said method comprising a combination of Triton X-114 partitioning and size separation techniques, amongst others. In particular, the *M. pneumoniae* polypeptide set forth in SEQ ID NO:2 is purified by Triton X-114 partitioning and SDS/polyacrylamide gel electrophoresis as described herein, in Examples 1 to 4 inclusive. Methods of purification of said polypeptide utilising additional or alternative procedures, for example reverse phase chromatography, ion-exchange chromatography, or affinity chromatography are also contemplated.

The present invention contemplates further a method of isolation of the polypeptide set forth in SEQ ID NO:1, said method comprising any combination of purification procedures selected from the list comprising chromatographic, phase separation, electrophoresis, ion-exchange chromatography, gel filtration, reverse-phase chromatography, SDS/polyacrylamide gel electrophoresis or detergent partitioning, amongst others. It will be known to those skilled in the art how to vary the above procedures.

A further aspect of the present invention provides a vaccine composition comprising a polypeptide component which comprises an isolated immunogenic polypeptide obtainable or derived from a species of Mycoplasma, or alternatively, a recombinant immunogenic polypeptide comprising an amino acid sequence similar or identical to said isolated immunogenic polypeptide, in combination with a pharmaceutically acceptable carrier or diluent.

Preferably, the polypeptide component of said vaccine composition is a polypeptide according to any of the foregoing embodiments described herein, in particular the *M. pneumoniae* or *M. genitalium* polypeptides set forth in SEQ ID NO:1, SEQ ID NO:2, SEQ ID NO: 4 or SEQ ID NO: 5 or a derivative, homologue or analogue thereof.

The vaccine composition of the present invention is effective in mediating an immune response when ingested, injected, or otherwise administered to a mammal. In a preferred embodiment, said vaccine induces humoral immunity against a *Mycoplasma spp.*, in particular *M. pneumoniae* or *M. genitalium*, when injected, or otherwise administered to a mammal. More preferably, said vaccine composition prevents the onset, development, or progression of symptoms associated with *M. pneumoniae* infection, for example atypical pneumonia, lung lesions, inflammatory reactions of the respiratory tract or central nervous system, amongst others.

The vaccine composition of present invention extends to vaccines in which the polypeptide component comprises a variant of the polypeptides referred to supra. The term "variant" as used herein shall be taken to include a mutant, derivative, part, fragment, analogue, or homologue of the amino acid sequence set forth in SEQ ID NO:1 or SEQ ID NO:2 or SEQ ID NO: 4 or SEQ ID NO: 5, which is at least about 30% similar, more preferably at least about 70% similar, still more preferably at least about 80% similar and even still more preferably at least about 99% similar to all, or a part, of the amino acid sequence set forth in SEQ ID NO:1 or SEQ ID NO:2 or SEQ ID NO: 4 or SEQ ID NO: 5.

In an alternative embodiment the present invention provides a vaccine composition comprising an isolated or recombinant immunogenic polypeptide which is obtainable from a species of Mycoplasma, in combination with a pharmaceutically acceptable carrier or diluent, wherein said polypeptide is further characterised by any of the following properties or is derived from a polypeptide having any of the following properties:

(I) it has a predicted molecular weight of approximately 16 kDa;

(ii) it has a molecular weight of approximately 110 kDa as determined by SDS/PAGE, or a predicted molecular weight of approximately 116 kDa;

(iii) it is a surface polypeptide in its native form;

(iv) it has adhesion properties in its native form; or (v) it comprises an amino acid sequence substantially as set forth in SEQ ID NO:1 or SEQ ID NO:2 or SEQ ID NO: 4 or SEQ ID NO: 5 or having at least 70% similarity to all or a part thereof.

In a particularly preferred embodiment the present invention provides a recombinant vaccine, which vaccine comprises:

(I) a recombinant polypeptide comprising a sequence of amino acids as set forth in either SEQ ID NO:1 or SEQ ID NO:2 or SEQ ID NO: 4 or SEQ ID NO: 5 or a derivative, homologue or analogue thereof which is capable of mediating an immune response against *M. pneumoniae* or *M. genitalium;* and (ii) a pharmaceutically acceptable carrier or diluent;

According to this aspect of the invention, said vaccine mediates an immune response against *Mycoplasma spp.*, in particular *M. pneumoniae* or *M. genitalium*, when the vaccine is injected, or otherwise administered to a mammal, for example a primate such as a human or monkey or a rodent such as a mouse, rat, hamster or guinea pig. Still more preferably, the vaccine induces humoral immunity against *M. pneumoniae* or *M. genitalium* in said mammal. Even still more preferably, the recombinant vaccine of the present invention prevents the onset, development, or progression of symptoms associated with *M. pneumoniae* infection, for example atypical pneumonia, lung lesions, inflammatory reactions of the respiratory tract, or of the central nervous system, amongst others.

In a further preferred embodiment, the vaccine may also comprise an adjuvant to boost the immune response of an animal to the immunogenic polypeptide when the vaccine is administered to said animal.

A third aspect of the present invention provides a method of producing a vaccine composition which method comprises the steps of:

(I) diluting a substantially homogeneous form of a polypeptide immunogen comprising a *M. pneumoniae* or *M. genitalium* polypeptide according to any of the embodiments described herein, in particular the *M. pneumoniae* polypeptide set forth in SEQ ID NO:1 or SEQ ID NO:2 or a derivative, homologue or analogue thereof or the *M. genitalium* polypeptide set forth in SEQ ID NO: 4 or SEQ ID NO: 5, in a pharmaceutically acceptable carrier or diluent; and (ii) optionally, combining said polypeptide immunogen or a derivative, homologue or analogue thereof with a physiologically acceptable adjuvant.

Preferably, the method according to this aspect of the invention comprises the further first step of preparing a substantially homogeneous form of a polypeptide immunogen comprising a *M. pneumoniae* polypeptide according to any of the embodiments described herein, in particular the *M. pneumoniae* polypeptide set forth in SEQ ID NO:1 or SEQ ID NO:2 or the *M. genitalium* polypeptide set forth in SEQ ID NO: 4 or SEQ ID NO: 5 or a derivative, homologue or analogue thereof, which is capable of mediating an immune response against *M. pneumoniae* or *M. genitalium.*

More preferably, said method of producing a vaccine composition comprises the further first step of culturing a micro-organism, bacterial cell, virus particle, fungal cell, insect cell, yeast cell, plant cell, or animal cell which comprises a nucleic acid molecule contained therein which encodes, or is complementary to a nucleic acid molecule which encodes a recombinant *M. pneumoniae* polypeptide immunogen according to any of the embodiments described herein for a time and under conditions sufficient for expression of said nucleic acid molecule to occur to produce said immunogen.

Even more preferably, said method comprises the further first step of transfecting, transforming or otherwise introducing said nucleic acid molecule into a micro-organism, bacterial cell, virus particle, fungal cell, yeast cell, insect cell, plant cell, or animal cell.

The term "mediating an immune response" as hereinbefore described is defined in its broadest context to include the elicitation of T-cell activation by a polypeptide, and/or the generation, by B-cells of antibodies which cross-react with one or more polypeptide immunogen molecules of the present invention.

According to these embodiments of the present invention, said polypeptide immunogen includes a polypeptide which comprises, mimics, or cross-reacts with a B cell or T cell epitope of any polypeptide according to the embodiments described herein or a derivative, homologue or analogue thereof.

Preferably, said polypeptide immunogen includes any polypeptide comprising a sequence of at least 10 amino acid residues in length, which are substantially the same as any part of the amino acid sequence set forth in SEQ ID NO:1 or SEQ ID NO:2 or SEQ ID NO:4 or SEQ ID NO: 5, or a derivative, analogue, or homologue thereof, as described supra.

Particularly preferred derivatives according to this embodiment are the derivatives of the 116 kDa. *M. pneumoniae* polypeptide (SEQ ID NO: 2) which are listed in Table 5. In a most particularly preferred embodiment, the derivative comprises amino acid residues 9 to 473 of SEQ ID NO: 2 or a homologue, analogue or derivative thereof.

A further aspect of the present invention provides an immunologically interactive molecule prepared against a polypeptide immunogen which comprises, cross-reacts or mimics a B-cell or T-cell epitope of an *M. pneumoniae* polypeptide, in particular a polypeptide comprising a sequence of amino acids set forth in SEQ ID NO:1 or SEQ ID NO:2 or a derivative, homologue or analogue thereof according to any of the embodiments described herein.

The term "immunologically interactive molecule" is herein defined as polyclonal or monoclonal antibodies, or functional derivatives thereof, for example Fabs, SCABS (single-chain antibodies) or antibodies conjugated to any enzyme, radioactive or fluorescent tag, the only requirement being that said immunologically interactive molecule is capable of binding to a polypeptide obtainable from *Mycoplasma spp.*, or a derivative, homologue or analogue thereof, or to a molecule which mimics the 3-dimensional structure of same. In the present context, it is preferred that an immunologically interactive molecule is capable of binding to a polypeptide which comprises a sequence of amino acids set forth in SEQ ID NO:1 or SEQ ID NO:2 or SEQ ID NO: 4 or SEQ ID NO: 5 or a derivative, homologue or analogue thereof, or a molecule which mimics the 3-dimensional structure of same.

Preferably, the immunologically interactive molecule of the present invention is prepared against an isolated or recombinant polypeptide of *M. pneumoniae* or *M. genitalium* according to any embodiment described herein.

Conventional methods can be used to prepare the immunologically interactive molecules. For example, by using a polypeptide of the present invention polyclonal antisera or monoclonal antibodies can be made using standard methods. As demonstrated in Examples 1 and 2 of the present invention, a mammal, (e.g., a mouse, hamster, or rabbit) can be immunized with an immunogenic form of the polypeptide which elicits an antibody response in the mammal. Techniques for conferring immunogenicity on a polypeptide include conjugation to carriers or other techniques well known in the art. For example, the polypeptide can be administered in the presence of adjuvant. The progress of immunization can be monitored by detection of antibody titres in plasma or serum. Standard ELISA or other immunoassay can be used with the immunogen as antigen to assess the levels of antibodies. Following immunization, antisera can be obtained and, if desired IgG molecules corresponding to the polyclonal antibodies may be isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. For example, the hybridoma technique originally developed by Kohler and Milstein (1975) as well as other techniques such as the human B-cell hybridoma technique (Kozbor et al., 1983), the EBV-hybridoma technique to produce human monoclonal antibodies (Cole et al., 1985), and screening of combinatorial antibody libraries (Huse et al., 1989). Hybridoma cells can be screened immunochemically for production of antibodies which are specifically reactive with the polypeptide and monoclonal antibodies isolated.

As with all immunogenic compositions for eliciting antibodies, the immunogenically effective amounts of the polypeptides of the invention must be determined empirically. Factors to be considered include the immunogenicity of the native polypeptide, whether or not the polypeptide will be complexed with or covalently attached to an adjuvant or carrier protein or other carrier and route of administration for the composition, i.e. intravenous, intramuscular, subcutaneous, etc., and the number of immunizing doses to be administered. Such factors are known in the vaccine art and it is well within the skill of immunologists to make such determinations without undue experimentation.

The term "antibody" as used herein, is intended to include fragments thereof which are also specifically reactive with a polypeptide which comprises, mimics, or cross-reacts with a B cell or T cell epitope of a Mycoplasma polypeptide according to the embodiments described herein, in particular a polypeptide set forth in SEQ ID NO:1 or SEQ ID NO:2 or SEQ ID NO: 4 or SEQ ID NO: 5 or a homologue, analogue or derivative thereof. Antibodies can be fragmented using conventional techniques and the fragments screened for utility in the same manner as described above for whole antibodies. For example, F(ab')2 fragments can be generated by treating antibody with pepsin. The resulting F(ab')2 fragment can be treated to reduce disulfide bridges to produce Fab' fragments.

It is within the scope of this invention to include any second antibodies (monoclonal, polyclonal or fragments of antibodies) directed to the first mentioned antibodies discussed above. Both the first and second antibodies may be used in detection assays or a first antibody may be used with a commercially available anti-immunoglobulin antibody.

The polyclonal, monoclonal or chimeric monoclonal antibodies can be used to detect the polypeptide of the invention or a derivative, homologue or analogue thereof in various biological materials, for example they can be used in an ELISA, radioimmunoassay or histochemical tests. Thus, the antibodies can be used to test for binding to a polypeptide of the invention, or a derivative, homologue or analogue thereof in a sample and in order to determine B cell or T cell epitopes of same. Using methods described hereinbefore, polyclonal, monoclonal antibodies, or chimeric monoclonal antibodies can be raised to a polypeptide which comprises, mimics, or cross-reacts with a B cell or T cell epitope of the polypeptide of *M. pneumoniae* set forth in SEQ ID NO:1 or SEQ ID NO:2 or a polypeptide of *M. genitalium* set forth in SEQ ID NO: 4 or SEQ ID NO: 5 or a derivative, homologue or analogue thereof.

According to this embodiment of the present invention, an antibody molecule which binds to a polypeptide immunogen which comprises, mimics, or cross-reacts with a B cell or T cell epitope of a polypeptide of *M. pneumoniae* or *M. genitalium* according to the embodiments described herein, is contacted with a second polypeptide, preferably comprising a sequence of amino acids which is a subset of, or overlaps the amino acid sequence of the polypeptide against which the antibody was raised. Standard ELISA or other immunoassay is used to assess the relative binding of antibody to the derivative polypeptide molecule. Thus, a continuous and highly immunogenic B cell or T cell epitope may be identified as the smallest amino acid sequence present in both the first polypeptide and one or more derivative polypeptides, which is highly immunoreactive with said antibody. A polypeptide molecule may comprise more than one continuous B cell or T cell epitope. A highly immunogenic, discontinuous B cell or T cell epitope may thus be inferred as any possible combination of one or more continuous B cell or T cell epitopes of a *M. pneumoniae* polypeptide as hereinbefore described, in particular the *M. pneumoniae* polypeptide set forth in SEQ ID NO:1 or SEQ ID NO:2 or the *M. genitalium* polypeptide set forth in SEQ ID NO: 4 or SEQ ID NO: 5. According to this embodiment of the present invention, a discontinuous B cell or T cell epitope shall be taken to include a polymer of B cell or T cell epitopes, as hereinbefore described.

A wide range of immunoassay techniques are available as can be seen by reference to U.S. Pat. Nos. 4,016,043, 4,424,279 and 4,018,653. These, of course, include both single-site and two-site or "sandwich" assays of the non-competitive types, as well as in the traditional competitive binding assays. These assays also include direct binding of a labelled antibody to a target.

Sandwich assays are among the most useful and commonly used assays and are favoured for use in the present invention. A number of variations of the sandwich assay technique exist, and all are intended to be encompassed by the present invention. Briefly, in a typical forward assay, an unlabelled antibody is immobilised on a solid substrate and the sample to be tested brought into contact with the bound molecule. After a suitable period of incubation, for a period of time and under conditions sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule.

In this case, the first antibody is raised to a polypeptide immunogen which has the characteristics of a polypeptide according to the embodiments described herein.

The results may either be qualitative, by simple observation of the visible signal, or may be quantitated by comparing with a control sample containing known amounts of antigen. Variations on the forward assay include a simultaneous assay, in which both sample and labelled antibody are added simultaneously to the bound antibody. These techniques are well known to those skilled in the art, including any minor variations as will be readily apparent. In accordance with the present invention, the sample is one which may contain a synthetic polypeptide substantially the same as, or derived from the amino acid sequence set forth in SEQ ID NO:1 or SEQ ID NO:2 or SEQ ID NO: 4 and SEQ ID NO: 5, or the immunogenic B cell or T cell epitopes contained therein.

In the typical forward sandwich assay, a first antibody raised against a surface polypeptide of the present invention is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs, microplates or microplate wells, or any other surface suitable for conducting an immunoassay. The binding processes are well-known in the art and generally consist of cross-linking, covalent binding or adsorption. The polymer-antibody complex is washed in preparation of the test sample. An aliquot of the sample to be tested is then added to the solid phase complex and incubated for a period of time sufficient (e.g. 2–40 minutes) and under suitable conditions (e.g. 25° C.) to allow binding of any antigen present in the sample to the antibody. Following the incubation period, the reaction locus is washed and dried and incubated with a second antibody specific for a portion of the first antibody. The second antibody is linked to a reporter molecule which is used to indicate the binding of the second antibody to the antigen.

An alternative method involves immobilising the target molecules in the biological sample and then exposing the immobilised target to specific antibody which may or may not be labelled with a reporter molecule. Depending on the amount of target and the strength of the reporter molecule signal, a bound target may be detected by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognised, however, a wide variety of different conjugation techniques exist, which are readily available to the skilled artisan. Commonly used enzymes include horseradish perioxidase, glucose oxidase, β-galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and horseradish peroxidase. It is also possible to employ fluorogenic substrates which yield a fluorescent product rather than the chromogenic substrate noted above. In all case, the enzyme-labelled antibody is added to the first antibody-antigen complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of antigen which was present in the sample. The term "reporter molecule" also extends to use of cell agglutination or inhibition of agglutination such as red blood cells on latex beads, and the like.

Alternately, fluorescent compounds, such as fluorescein and rhodamine, may be chemically coupled to antibodies, without altering their binding capacity. When activated by illumination with light of a particular wavelength, the fluorochrome-labelled antibody adsorbs the light energy, inducing a state to excitability in the molecule, followed by emission of the light at a characteristic colour visually detectable with a light microscope. As in enzyme immunoassays (EIA), the fluorescent labelled antibody is allowed to bind to the first antibody-antigen complex. After washing off the unbound reagent, the remaining tertiary complex is then exposed to the light of the appropriate wavelength and the fluorescence observed indicates the presence of the antigen of interest. Immunofluorescence and EIA techniques are both very well established in the art and are particularly preferred for the present method. However, other reporter molecules, such as radioisotope, chemiluminescent or bioluminescent molecules, may also be employed. It will be readily apparent to the skilled technician how to vary the above assays and all such variations are encompassed by the present invention.

Accordingly, a further aspect of the present invention contemplates a method of detecting a polypeptide of Mycoplasma spp., in particular a polypeptide of *M. pneumoniae* or *M. genitalium* in serum, mucus, tissue extract, or other biological fluid comprising the steps of contacting said serum, mucus, tissue extract or other biological fluid to be tested with an antibody which recognises said polypeptide a part thereof for a time and under conditions sufficient for an antibody:polypeptide complex to form and subjecting said complex to a detecting means. The latter complex may be detected by the antibody or polypeptide, preferably the antibody, having attached thereto a reporter molecule, or by addition of a second antibody labelled with a reporter molecule.

In a particularly preferred embodiment, this aspect of the present invention contemplates a method of detecting a polypeptide of *M. pneumoniae* which comprises a sequence of amino acids set forth in SEQ ID NO:1 or SEQ ID NO:2 or a derivative, homologue or analogue thereof.

Accordingly, the present invention also contemplates a kit of the rapid and convenient assay for a polypeptide of Mycoplasma spp., in particular a polypeptide of *M. pneumoniae* or *M. genitalium* in serum, mucus, tissue extract, or other biological fluid.

Those skilled in the art will be aware that the subject kit is also useful for the purpose of determining the presence of whole cells of said Mycoplasma ssp.

The kit is compartmentalized to receive several first containers adapted to contain a polypeptide according to any of the embodiments hereinbefore described or a B cell or T cell epitope thereof in recombinant or synthetic form, and several second containers adapted to contain an antibody which recognises said polypeptide or B cell or T cell epitope thereof, wherein said antibody is optionally labelled with a reporter molecule capable of producing a detectable signal as hereinbefore described. If the antibody of the second container is not labelled with a reporter molecule, then there are also provided several third containers which contain a second antibody which recognises the first antibody and is conjugated to a reporter molecule. If the reporter molecule is an enzyme, then several fourth containers are provided which contain a substrate molecule for said enzyme to facilitate detection of the enzyme linked to a polypeptide-:antibody complex, or to a polypeptide:antibody:antibody complex when a second antibody has been used. The reporter molecule used in this kit may also be a radioisotope, a fluorescent molecule, or bioluminescent molecule, amongst others. Optionally, the first, second, third and fourth containers of said kit may be colour-coded for ease of use.

In an exemplified use of the subject kit, a control reaction is carried out in which the contents of the first container are contacted with the contents of the second container for a time and under conditions sufficient for an antibody-:polypeptide complex to form in said first container. At the same time the sample to be tested is contacted with the contents of the second container for a time and under conditions sufficient for an antibody:polypeptide complex to form in said second container. If the antibody of the second container provided is not labelled with a reporter molecule, then the complexes produced in said first and second containers are contacted with the antibody of the third container for a time and under conditions sufficient for a tertiary polypeptide:antibody:antibody complex to form. The polypeptide:antibody complex or polypeptide:antibody:antibody complex is then subjected to a detecting means as hereinbefore described. In analysing the results obtained using said kit, the control reaction carried out in said first container should always provide a positive result upon which to compare the results obtained in said second container which contains the test sample.

A further aspect of the present invention provides a method of assaying for the presence of antibodies against a Mycoplasma ssp. in a mammal such as a human, said method comprising contacting a biological sample from said mammal with an isolated or recombinant polypeptide comprising an amino acid sequence as set forth in SEQ ID NO:1 or SEQ ID NO:2 or SEQ ID NO:4 or SEQ ID NO:5 for a time and under conditions sufficient to enable an antibody-antigen complex formation to occur.

In a preferred embodiment, said antibody-antigen complex is subsequently subjected to a detecting means.

In one embodiment, the antibodies present in a biological sample obtained from an individual are capable of binding to one or more epitopes of a *M. pneumoniae* polypeptide set forth in SEQ ID NO:1 or SEQ ID NO:2 or the *M. genitalium* sequences set forth in SEQ ID NO:4 or SEQ ID NO:5 or a homologue, analogue or derivative thereof. Preferably, the antibodies present in such a biological sample are capable of binding to one or more epitopes which in their native state are localised on the surface of Mycoplasma spp. in particular *M. pneumoniae* or *M. genitalium* for example a surface epitope of the surface polypeptide which is set forth in SEQ ID NO:2.

In a more preferred embodiment, the present invention provides a method of assaying for the presence of antibodies against a Mycoplasma ssp. in a human individual, said method comprising contacting a biological sample obtained from said individual with an isolated or recombinant polypeptide as set forth in SEQ ID NO:2 for a time and under conditions sufficient to enable an antibody-antigen complex formation to occur and subjecting said antibody-antigen complex to a detecting means.

Even more particularly, the recombinant polypeptide comprises an amino acid sequence substantially the same as amino acid residues 9 to 473 of SEQ ID NO:2 or a homologue, analogue or derivative thereof.

According to these embodiments of the invention, it will be understood in the art that a positive result will occur when the biological sample assayed contains antibodies against said polypeptide or a derivative, homologue or analogue thereof. Those skilled in the art will be aware that such antibodies will usually have arisen as a result of infection of the individual from whom the biological sample is derived by Mycoplasma ssp., in particular *M. pneumoniae* or *M. genitalium.*

Any biological sample containing antibodies is sufficient for the present purposes, the only requirement being that said biological sample contains sufficient antibodies against a surface polypeptide of Mycoplasm spp., in particular a surface polypeptide of *M. pneumoniae* or *M. genitalium*, to enable the detection of the antibody-antigen complex.

Preferably, the biological sample is selected from the list comprising blood or blood products, mucus, respiratory epithelium, tissue of the upper respiratory tract, cerebrospinal fluid or tissue of the central nervous system, amongst others. If difficulties are obtained in detection of an antibody-antigen complex, it is possible to purify or concentrate the immunoglobulin fraction present in said biological sample, using any one or more standard procedures known to those skilled in the relevant art, prior to using the method hereinbefore described. The present invention extends to the use of any immunoglobulin fractions, or partially-purified antibody preparation which is obtained for the purpose of detecting antibodies as described herein.

It will also be known to those skilled in the art that the polypeptide used to detect said antibodies present in a biological sample may contain amino acid substitutions, deletions, insertions, or other modifications including the addition of enzyme molecules, radioisotopes or fluorescent tags, amongst others, which may be useful in assisting the detection of the antibody-antigen complex formed according to this aspect of the invention. The present invention therefore extends to the use of derivatives, homologues or analogues of the subject polypeptides used in the performance of the assay described according to this aspect of the invention.

The method described herein is at least useful for the purpose of determining whether said mammal has been, at the time a biological sample was taken, infected with a microorganism belonging to the genus Mycoplasma, in particular *M. pneumoniae* such that antibodies to said microorganism have been produced in response to infection.

Accordingly, an alternative embodiment of the present invention provides a method of detection of Mycoplasma infection in an individual, said method comprising contacting a biological sample obtained from said individual with an isolated or recombinant polypeptide as set forth in SEQ ID NO:1 or SEQ ID NO:2 or SEQ ID NO:4 or SEQ ID NO:5 or a derivative, homologue or analogue thereof, for a time and under conditions sufficient to enable an antibody-antigen complex formation to occur and subjecting said antibody-antigen complex to a detecting means and wherein said method is an immunoassay.

According to this embodiment of the invention, said immunoassay may be an ELISA, radioimmunoassay, histochemical test or sandwich assay.

According to the methods described in this aspect of the invention, the recombinant polypeptide is immobilised on a solid substrate and the biological sample containing antibodies against a polypeptide of Mycoplasma, in particular *M. pneumoniae* or *M. genitalium*, is brought into contact with the bound antigen. After a suitable period of incubation, for a period of time and under conditions sufficient to allow formation of an antibody-antigen complex, a second antibody which is specific for the bound antibody and labelled with a reporter molecule capable of producing a detectable signal, may be added, and the reaction mixture incubated, allowing sufficient time for the formation of an antigen-antibody-antibody complex. Any reacted material is washed away and the presence of antibodies in the biological sample is determined by observation of a signal produced by the reporter molecule as hereinbefore defined. Variations to the method described are numerous and will be apparent to those skilled in the art. The present invention extends to all variations of the method described herein.

Accordingly, the present invention also contemplates a kit for the rapid and convenient assay of infection by Mycoplasma spp., in particular *M. pneumoniae* in an individual comprising, in a first compartment several first containers adapted to contain the isolated polypeptide set forth in SEQ ID NO:1 or SEQ ID NO:2 or SEQ ID NO:4 or SEQ ID NO:5 or a derivative, homologue or analogue thereof in recombinant or synthetic form and optionally adsorbed thereto, and several second containers adapted to contain an antibody which recognises said polypeptide or a B cell or T cell epitope thereof, wherein said antibody is optionally labelled with a reporter molecule capable of producing a detectable signal as hereinbefore described. There are also provided several third containers which contain a second antibody which recognises the first antibody and is conjugated to a reporter molecule. If the reporter molecule is an enzyme, then several fourth containers are provided which contain a substrate molecule for said enzyme to facilitate detection of the enzyme linked to a polypeptide:antibody complex, or to a polypeptide:antibody:antibody complex when a second antibody has been used. The reporter molecule used in this kit may also be a radio-isotope, a fluorescent molecule, or bioluminescent molecule, amongst others. Optionally, the first, second, third and fourth containers of said kit may be colour-coded for ease-of use.

In an alternative embodiment, the kit may be contained in a package which comprises microtitre wells in one section, in which reactions may be performed. Accordingly, in one embodiment, the microtitre wells may be the equivalent of the first compartment hereinbefore described and contain the polypeptide set forth in SEQ ID NO:1 or SEQ ID NO:2 or SEQ ID NO:4 or SEQ ID NO:5 or a derivative, homologue or analogue thereof, adsorbed thereto.

In an exemplified use of the subject kit, the contents of the first container may be bound to a microtitre well contained in the package, if not provided in a format where said contents are already adsorbed to said microtitre well, and a biological sample to be tested is added and incubated for a time and under conditions sufficient for an antigen-antibody complex to form in said microtitre well. Following a washing step to remove unbound antibodies and other unbound protein, the contents of the third container are added to the antigen-antibody complex contained in the microtitre well and the reaction allowed to proceed for a time, and under conditions sufficient to allow the formation of the tertiary antigen-antibody-antibody complex. A positive control reaction may be performed in which the contents of the second container are added to the contents of the first container for a time and under conditions suitable for the formation of an antigen-antibody complex. If the antibody of the second container is not labelled with a reporter molecule, then the contents of the third container may be added for a time and under conditions suitable for the formation of a tertiary antigen-antibody-antibody complex to form. The tertiary antigen-antibody-antibody complexes of the control reaction and the test sample are the subjected to a detecting means. Alternatively, if the contents of the second container are labelled with a reporter molecule the antigen-antibody complex of the control reaction may be subjected directly to a detecting means. The means of detection of a secondary antigen-antibody or a tertiary antigen-antibody-antibody complex are numerous, as hereinbefore described and will be known to those skilled in the art. Where said means is an enzyme reaction, the contents of the fourth container are added to said secondary or tertiary complex thus formed for a time and under conditions suitable to enable the enzyme reaction to occur. In analysing the results obtained using the subject kit, the control reaction should always provide a positive result for comparison to the results obtained for the test sample. A positive result is indicative of infection by Mycoplasma spp., in particular *M. pneumoniae* or *M. genitalium.*

A further aspect of the present invention provides an isolated nucleic acid molecule comprising a sequence of nucleotides which encodes, or is complementary to a nucleic acid molecule which encodes a Mycoplasma spp. polypeptide according to any of the embodiments hereinbefore described.

In a related embodiment, the present invention provides an isolated nucleic acid molecule which encodes, or is complementary to a nucleic acid molecule which encodes a polypeptide which comprises, mimics, or cross-reacts with a B cell or T cell epitope of a Mycoplasma spp. polypeptide according to any of the embodiments hereinbefore described.

More particularly, in one embodiment the present invention provides an isolated nucleic acid molecule which encodes, or is complementary to a nucleic acid molecule which encodes a polypeptide or a derivative, homologue or analogue thereof which is obtainable from a *M. pneumoniae* wherein said polypeptide has a molecular weight of approximately 110 kDa as determined by SDS/PAGE, or a predicted molecular weight of approximately 116 kDa, is a surface polypeptide and has adhesion properties.

Preferably, said nucleic acid molecule further comprises a sequence of nucleotides substantially the same as, or at least 40% similar to nucleotides 655–4071 of the sequence set forth in SEQ ID NO:3 or a complement or homologue, analogue or derivative thereof. More preferably, said nucleic acid molecule is substantially the same as or at least 40% similar to nucleotides 762–3851 of SEQ ID NO:3 or a complement thereof.

In an alternative embodiment, the present invention provides a nucleic acid molecule which encodes or is complementary to a nucleic acid molecule which encodes a polypeptide or a derivative, homologue or analogue thereof obtainable from *M. pneumoniae* with a predicted molecular weight of approximately 16 kDa.

Preferably, said nucleic acid molecule further comprises a sequence of nucleotides substantially the same as, or at least 40% similar to nucleotides 1–761 of the sequence set forth in SEQ ID NO:3 or a complement or a homologue, analogue or derivative thereof. More preferably, said nucleic acid molecule is substantially the same as or at least 40% similar to nucleotides 250–654 of SEQ ID NO:3 or a complement or a homologue, analogue or derivative thereof.

In a further embodiment of the present invention, there is provided a nucleic acid molecule which comprises a sequence of nucleotides at least 40% sequence similar to the nucleotide sequence set forth in SEQ ID NO:3, or a complementary strand, or part thereof. Preferably, the percentage similarity is at least 60–65%. More preferably, the percentage similarity is at least 70–75%. Yet still more preferably, the percentage similarity is at least 80–90%, including at least 91% or 93% or 95%.

For the present purpose, "homologues" of a nucleotide sequence shall be taken to refer to an isolated nucleic acid molecule which is substantially the same as the nucleic acid molecule of the present invention or its complementary nucleotide sequence, notwithstanding the occurrence within said sequence, of one or more nucleotide substitutions, insertions, deletions, or rearrangements.

"Analogues" of a nucleotide sequence set forth herein shall be taken to refer to an isolated nucleic acid molecule which is substantially the same as a nucleic acid molecule of the present invention or its complementary nucleotide sequence, notwithstanding the occurrence of any non-nucleotide constituents not normally present in said isolated nucleic acid molecule, for example carbohydrates, radiochemicals including radionucleotides, reporter molecules such as, but not limited to DIG, alkaline phosphatase or horseradish peroxidase, amongst others.

"Derivatives" of a nucleotide sequence set forth herein shall be taken to refer to any isolated nucleic acid molecule which contains significant sequence similarity to said sequence or a part thereof. Generally, the nucleotide sequence of the present invention may be subjected to mutagenesis to produce single or multiple nucleotide substitutions, deletions and/or insertions. Nucleotide insertional derivatives of the nucleotide sequence of the present invention include 5' and 3' terminal fusions as well as intra-sequence insertions of single or multiple nucleotides or nucleotide analogues. Insertional nucleotide sequence variants are those in which one or more nucleotides or nucleotide analogues are introduced into a predetermined site in the nucleotide sequence of said sequence, although random insertion is also possible with suitable screening of the resulting product being performed. Deletional variants are characterised by the removal of one or more nucleotides from the nucleotide sequence. Substitutional nucleotide variants are those in which at least one nucleotide in the sequence has been removed and a different nucleotide or nucleotide analogue inserted in is place.

In yet another embodiment, the present invention provides a nucleic acid molecule which hybridises under at least low stringency conditions, preferably under moderate stringency conditions, and more preferably under high stringency conditions, to the nucleic acid molecule set forth in SEQ ID NO:3, or to a complementary strand, or a part thereof.

For the purposes of defining the level of stringency, a low stringency is defined herein as being a hybridisation and/or a wash carried out in 6×SSC buffer, 0.1% (w/v) SDS at 28° C. or alternatively, in 6×SSC buffer, 0.5% (w/v) SDS at 60° C. A moderate stringency is defined herein as being a hybridisation and/or a wash carried out in 2×SSC buffer, 0.1% (w/v) SDS at 65° C. A high stringency is defined as being a hybridisation and/or wash carried out in 0.1% SSC buffer, 0.1% (w/v) SDS. The conditions for varying the stringency of hybridisation reactions are well-known to those skilled in the art. Generally, the stringency is increased by reducing the concentration of SSC buffer, and/or increasing the concentration of SDS and/or increasing the temperature of the hybridisation and/or wash.

Conditions for hybridisations and washes are well understood by one normally skilled in the art. For the purposes of clarification, (to parameters affecting hybridisation between nucleic acid molecules), reference is found in pages 2.10.8 to 2.10.16. of Ausubel et al. (1987), which is incorporated herein by reference.

In yet still another embodiment, the present invention provides an isolated nucleic acid molecule which:

(i) encodes or is complementary to a sequence which encodes a Mycoplasma spp. polypeptide with a predicted molecular weight of approximately 16 kDa or 116 kDa, preferably the *M. pneumoniae* polypeptide set forth in SEQ ID NO:1 or SEQ ID NO:2; and (ii) hybridises under at least low stringency conditions, preferably under moderate stringency conditions, and more preferably under high stringency conditions, to the nucleic acid molecule set forth in SEQ ID NO:3, or to a complementary strand, or a part thereof.

The genetic sequences which encodes a Mycoplasma spp. polypeptide according to any of the embodiments hereinbefore described, in particular a genetic sequence which encodes or is complementary to a genetic sequence which encodes the polypeptides set forth in SEQ ID NO:1 or SEQ ID NO:2, may correspond to the naturally occurring sequence or may differ by one or more nucleotide substitutions, deletions and/or additions. Accordingly, the present invention extends to genes encoding said Mycoplasma polypeptides or derivatives, homologues or analogues thereof, or nucleic acid molecules which are at least useful as genetic probes, or primer sequences in the enzymatic or chemical synthesis of said gene, or in the generation of immunologically interactive recombinant molecules as hereinbefore described.

In a particularly preferred embodiment, the genetic sequences of the present invention are employed to identify and isolate similar genes, form any species of Mycoplasm, for example *M. pneumoniae, M. genitalium*, or *M. gallisepticum* amongst others, and from other organisms.

According to this aspect of the invention, there is provided an oligonucleotide molecule of at least 10 nucleotides, preferably at least 20 nucleotides and more preferably at least 50 nucleotides in length capable of hybridising under low stringency conditions to part of the nucleotide sequence, or to a complement of the nucleotide sequence set forth in SEQ ID NO:3.

The present invention clearly contemplates a method for identifying a genetic sequence which is related to the sequence set forth in SEQ ID NO:3, said method comprising contacting genomic DNA, or mRNA, or cDNA, or parts, or fragments thereof, or a source thereof, with a hybridisation effective amount of a nucleic acid molecule comprising a sequence of nucleotides set forth in SEQ ID NO:3 or a derivative, homologue, analogue or complement thereof and then detecting said hybridisation.

The related genetic sequence may be in a recombinant form, in a bacterial cell, virus particle, bacteriophage particle, yeast cell, fungal cell, insect cell, animal cell, or a plant cell. Preferably, the related genetic sequence originates form a species of Mycoplasma, in particular *M. pneumoniae, M. gallisepticum, M. pentrans, M. iowae, M. muris, M. urealyticum, M. pirum, M. imitans* or *M. genitalium*, amongst others. In addition, the related genetic sequence may be bound to a support matrix, for example nylon, nitrocellulose, polyacrylamide, agarose, amongst others.

Preferably, the latter genetic sequence is labelled with a reporter molecule capable of giving an identifiable signal (e.g. a radioisotope such as $^{32}P$ or $^{35}S$ or a biotintylated molecule).

An alternative method contemplated in the present invention involves hybridising two nucleic acid primer molecules of at least 10 nucleotides in length to a nucleic acid "template molecules", said template molecule herein defined as a "mycoplasma immunogen genetic sequence", "nycoplasma-like immunogen genetic sequence", or a functional part thereof, or its complementary sequence. Specific nucleic acid molecule copies of said template molecule are amplified enzymatically in a polymerase chain reaction, a technique that is well known to one skilled in the art.

Preferably, the nucleic acid primer molecules or molecule effective in hybridisation is contained in an aqueous mixture of other nucleic acid primer molecules. More preferably, the nucleic acid primer molecules are in a substantially pure form.

According to this embodiment of the present invention, the nucleic acid primer molecules are derived from opposite DNA strands of a genetic sequence of Mycoplasm sp., in particular *M. pneumoniae*, which encodes a polypeptide according to any of the embodiments hereinbefore described. Preferably, the nucleic acid primer molecules comprise any nucleotide sequence of at least 10 nucleotides preferably at least 20 nucleotides, more preferably at least 50 nucleotides in length, wherein the nucleotide sequence of one primer molecule is contained within the nucleotide sequence set forth in SEQ ID NO:3 and wherein the nucleotide sequence of the other primer molecule is the complement of the nucleotide sequence set forth in SEQ ID NO:3.

The present invention also contemplates the use of degenerate inosine-containing primer molecules which encode, or are complementary to a nucleic acid sequence which encodes, an amino acid sequence which is at least 70% identical to a part of the amino acid sequence set forth in SEQ ID NO:1 or SEQ ID NO:2.

The present invention further contemplates the use of a single primer molecule as hereinbefore described in combination with a non-specific primer molecule to amplify genetic sequences related to the nucleotide sequence set forth in SEQ ID NO:3.

The mycoplasma immunogen genetic sequence or mycoplasma-like immunogen genetic sequence may be in a recombinant form, in a bacterial cell, virus particle, bacteriophage particle, fungal cell, yeast cell, insect cell, animal cell, or a plant cell. Preferably, the related genetic sequence originates from Mycoplasma spp., for example *M. pneumoniae, M. genitalium, M. penetrans, M. iowae, M. muris, M. urealyticum, M. pirum, M. imitans* or *M. gallisepticum* amongst others. Furthermore, said genetic sequence may be in a crude cellular homogenate, or in a substantially purified form. Methods for the purification of genetic sequences from viral and cellular material are well known to a person skilled in the art.

The present invention extends to the detection of a nucleic acid molecule which encodes a polypeptide of Mycoplasm spp., in particular a polypeptide of *M. pneumoniae*, wherein said polypeptide is according to any of the embodiments hereinbefore described and wherein said nucleic acid molecule is present in serum, mucus, tissue extract, or other biological fluid. In a particularly preferred embodiment, said method is directed to the detection of the nucleotide sequence set forth in SEQ ID NO:3 or its complement, or a derivative, homologue or analogue thereof. Accordingly, said method is useful for the purpose of detecting the micro-organism Mycoplasma spp., in particular *M. pneumoniae* in said serum, mucus, tissue extract, or biological fluid.

The present invention clearly contemplates a kit for the rapid detection of the micro-organism Mycoplasma spp., in particular *M. pneumoniae* in a biological sample, said kit being compartmentalized to contain in a first compartment, one or more nucleic acid molecules which encode, or are complementary to a nucleic acid molecule which encodes a polypeptide of Mycoplasma spp., in particular a polypeptide of *M. pneumoniae* as hereinbefore described in embodiment. In a particularly preferred embodiment, the first compartment is adapted to contain one or more nucleic acid molecules which are substantially identical or at least 70% identical to the nucleotide sequence set forth in SEQ ID NO:3 or its complement or a derivative, homologue or analogue thereof.

The embodiments hereinbefore described do not extend to polypeptides or genetic sequences per se from *M. genitalium* or *M. gallisepticum* amongst others, however such embodiments do encompass the immunogenic properties and applications therefor of an immunogen comprising said polypeptide or encode by said genetic sequence.

The nucleic acid molecule of the present invention is capable of being expressed in a bacterial, yeast, animal or plant cell for the purpose of producing a polypeptide component of a vaccine composition as hereinbefore described.

Accordingly, yet still another aspect of the invention provides a genetic construct comprising a sequence of nucleotides which encodes, or is complementary to a nucleotide sequence which encodes a Mycoplasma spp. polypeptide as hereinbefore described in any embodiment, in particular the *M. pneumoniae* polypeptide set forth in SEQ ID NO:1 or SEQ ID NO:2, or a derivative, homologue or analogue thereof.

In an alternative embodiment, the genetic construct of the present invention comprises a sequence of nucleotides which encodes, or is complementary to a nucleotide sequence which encodes a polypeptide which comprises one or more immunogenic B cell or T cell epitopes which mimic, or cross-react, with a B cell or T cell epitope of a Mycoplasma spp. polypeptide as hereinbefore described in any embodiment, in particular the *M. pneumoniae* polypeptide set forth in SEQ ID NO:1 or SEQ ID NO:2.

In a preferred embodiment of the present invention, said genetic construct comprises a sequence of nucleotides which is at least 40% similar to the nucleotide sequence set forth in SEQ ID NO:3, or its complementary nucleotide sequence, or a derivative, homologue or analogue thereof. More preferably, the percentage similarity to the nucleotide sequence set forth in SEQ ID NO:3 is at least 60–65%, still more preferably at least 70–75%, even still more preferably at least 80–90%, including at least 91% or 93% or 95%.

Optionally, the nucleic acid molecule is operably linked to a promoter sequence, thereby regulating expression of said nucleic acid molecule in a virus particle, prokaryotic cell, or eukaryotic cell. It is understood in the art that viruses, including bacteriophage, utilise the transcriptional machinery of their host cell and thus, in order to achieve expression of a genetic construct in said virus it is necessary to use a promoter sequence that is capable of regulating expression in said host cell, whether a prokaryotic or a eukaryotic cell.

According to this embodiment of the present invention, a preferred promoter is one which is capable of expression in a eukaryotic cell, such as a fungal cell, insect cell, plant cell or an animal cell. It is known in the art that a promoter sequence is selected according to the specific purpose, for example the mode of gene regulation required. Promoters active in eukaryotic cells are numerous and described in the literature. More preferably, said promoter sequence regulates expression in a prokaryotic cell, for example the *Escherichia coli* lac promoter, or tac promoter sequences, amongst others. Additional promoters which are active in prokaryotic cells are also described in the literature.

The genetic construct optionally further comprises a terminator sequence. For the purposes of exemplification only, a suitable terminor sequence is the nopaline synthese gene terminator, or the octopine synthase gene terminator, amongst others.

The term "terminator" refers to a DNA sequence at the end of a transcriptional unit which signals termination of transcription. Terminators are 3'-non-translated DNA sequences. In the genetic material of eukaryotic organisms, terminator sequences contain a polyadenylation signal which facilitates the addition of polyadenylated (i.e. poly (A)) sequences to the 3'-end of a primary transcript. Many terminators are known and described in the literature. They may be isolated from genes of bacteria, fungi, viruses, animals and/or plants.

Reference herein to a "promoter" is to be taken in its broadest context and includes the transcriptional regulatory sequences of classical genomic gene, for example a TATA box which may be required for accurate transcription initiation, or a CCAAT box sequence and additional regulatory elements (i.e. upstream activating sequences, enhancers and silencers) which may alter gene expression in response to developmental and/or external stimuli, or in a tissue-specific manner. A promoter is usually, but not necessarily, positioned upstream or 5', of a structural gene, the expression of which it regulates. Furthermore, the regulatory elements comprising a promoter are usually positioned within 2 kb of the start site of transcription of the gene.

In the present context, the term "promoter" is also used to describe a recombinant, synthetic or fusion molecule, or derivative which confers, activates or enhances the expression of a nucleic acid molecule which encodes, or is complementary to a nucleic acid molecule which encodes the immunogenic polypeptides of the present invention. Preferred promoters may contain additional copies of one or more specific regulatory elements, to further enhance expression and/or to alter the spatial expression and/or temporal expression of the same nucleic acid molecule. For example, regulatory elements which confer copper inducibility may be placed adjacent to a heterologous promoter sequence, thereby conferring copper inducibility on the expression of said nucleic acid molecule.

Placing a nucleic acid molecule under the regulatory control of a promoter sequence means positioning the said molecule such that expression is controlled by the promoter sequence. Promoters are generally positioned 5' (upstream) to the genes that they control. In the construction of heterologous promoter/structural gene combinations it is generally preferred to position the promoter at a distance from the gene transcription start site that is approximately the same as the distance between that promoter and the gene it controls in its natural setting, i.e., the gene from which the promoter is derived. As is known in the art, some variation in this distance can be accommodated without loss of promoter function. Similarly, the preferred positioning of a regulatory sequence element with respect to a heterologous gene to be placed under its control is defined by the positioning of the element in its natural setting, i.e., the genes from which it is derived. Again, as is known in the art, some variation in this distance can also occur.

Examples of promoters suitable for use in genetic constructs of the present invention include viral, fungal, bacterial, animal and plant derived promoters. The promoter may regulate the expression of the said molecule constitutively, or differentially with respect to the tissue in which expression occurs or, with respect to the developmental stage at which expression occurs, or in response to external stimuli such as physiological stresses, or plant pathogens, or metal ions, amongst others.

The genetic constructs of the present invention are particularly useful for the production of the polypeptide immunogen component of a vaccine composition, as hereinbefore described.

According to this embodiment of the present invention, a recombinant DNA molecule encoding an immunogenic polypeptide of the present invention as hereinbefore described in any embodiment, and/or a genetic construct comprising the same, may be introduced into a bacterial, fungal, plant, or animal cell producing a "transgenic organism", by various techniques known to those skilled in the art. The technique used for a given organism or specific type of tissue depends on the known successful techniques. Means for introducing recombinant DNA into a cell include, but are not limited to, transformation (Paszkowski et al., 1984), electroporation (Fromm et al., 1985), or microinjection of the DNA (Crossway et al., 1986), or specifically where said cell is a plant cell, by T-DNA-mediated transfer from Agrobacterium to the plant tissue.

Once introduced into a cell, the expression of the introduced gene may be assayed in a transient expression system, or it may be determined after selection for stable integration within the host genome.

A still further aspect of the present invention extends to a transgenic organism such as a plant, or a mammal, carrying the genetic constructs described herein. The present invention further extends to the progeny of said transgenic organism.

For the purposes of exemplification only, the present invention is further described by the following Figures and Examples.

In the Figures:

FIG. 1 is a photographic representation of an SDS/polyacrylamide gel of *M. pneumoniae* proteins partitioned using Triton X-114. Lane 1, molecular weight protein markers; lane 2, Triton X-114 detergent phase polypeptides; lane 3, Triton X-114 aqueous phase polypeptides; lane 4, whole cell proteins. Arrows indicate the 110 kDa Mycoplasma polypeptide (upper arrow) and a 70 kDa Mycoplasma polypeptide (lower arrow) enriched in the detergent phase.

Figure 4:
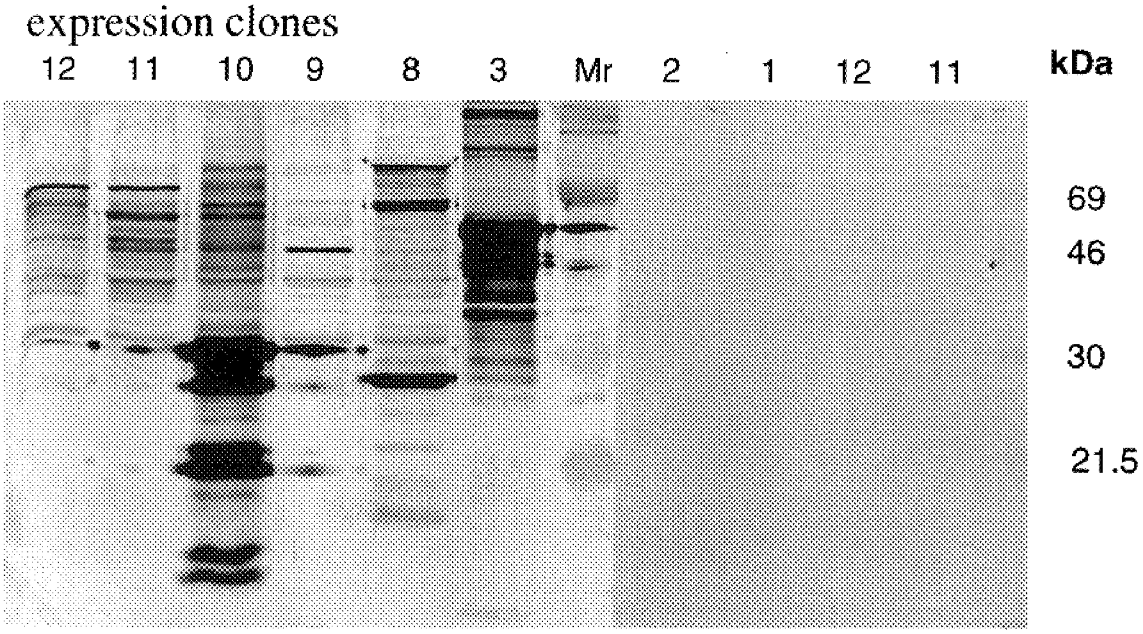

FIG. 4 is a photographic representation of a western blot of whole cell lysates obtained from immuno-positive clones expressing the *M. pneumoniae* 110 kDa polypeptide. The number at the top of each lane refers to the clone number, Mr, molecular weight marker. The blot was probed with antisera raised against the 110 kDa (116 kDa) polypeptide of *M. pneumoniae*.

Figure 5:
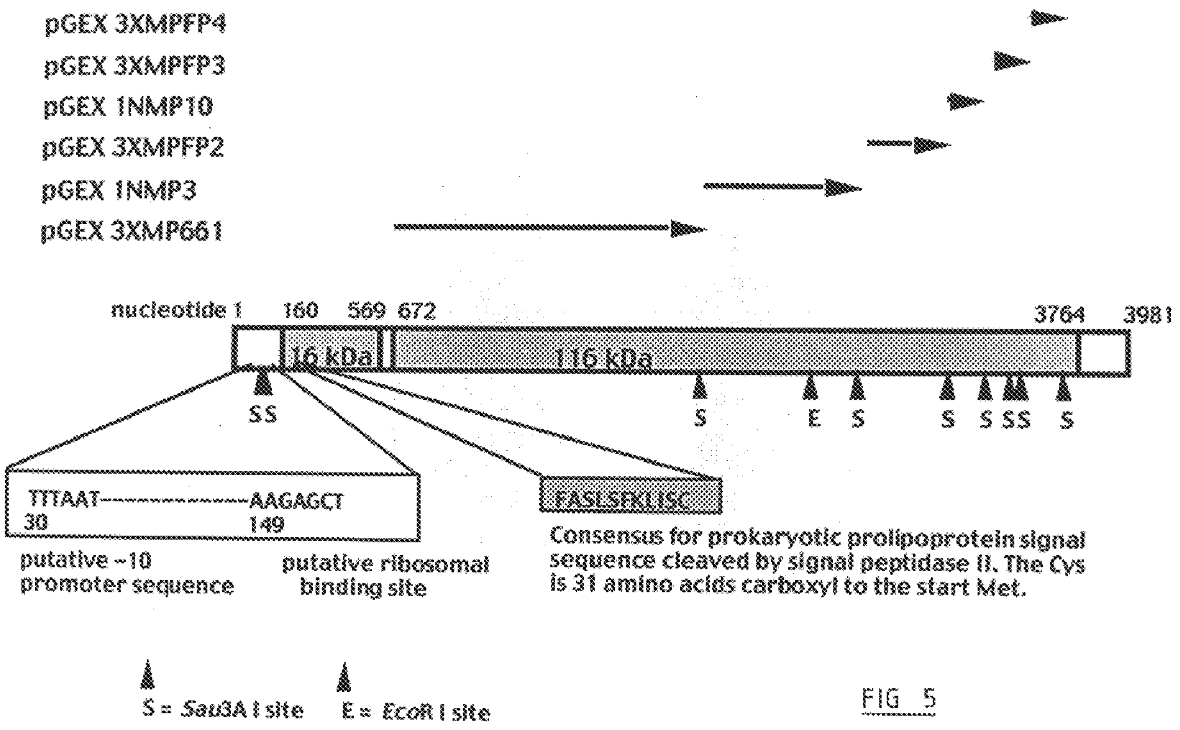

FIG. 5 is a schematic representation of the EcoRI fragment comprising the open reading frames encoding 16 kDa and 116 kDa *M. pneumoniae* polypeptides, showing the positions of the consensus Shine-Dalgamo sequence (AAGAGCT), consensus prolipoprotein signal peptidase II cleavage site (FASLSFKLISC), Sau3AI (S) and EcoRI (E) cleavage sites. Above the representation of the EcoRI fragment is a schematic representation showing the aligned Sau3AI fragments used to produce the expression vectors pGEX 3XMPFP4, pGEX 3XMPFP3, pGEX 1NMP10, pGEX 3XMPFP2, pGEX 1NMP3 and pGEX 3XMP661.

Figure 6:
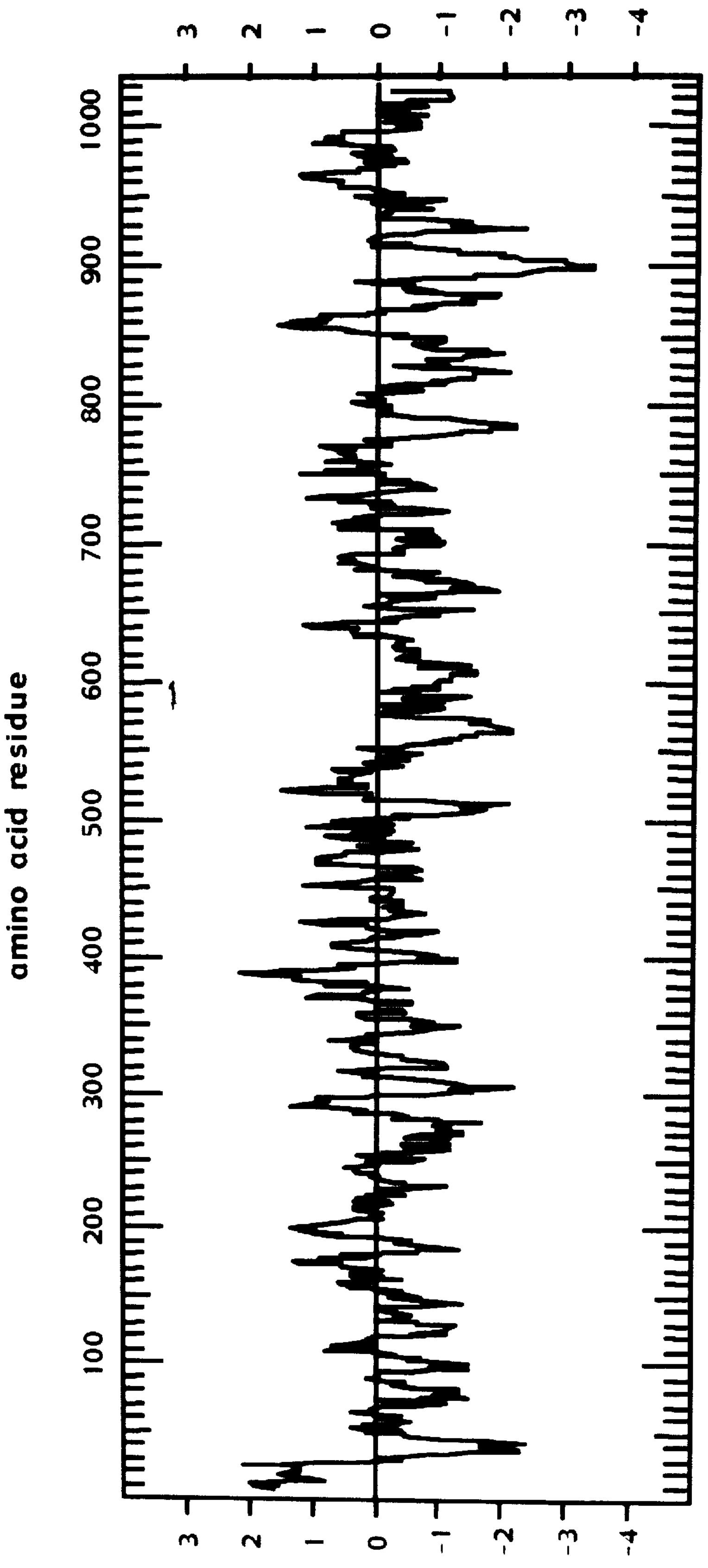

FIG. 6 is a graphical representation of a hydropathy plot of the 116 kDa *M. pneumoniae* polypeptide.

Figure 7:
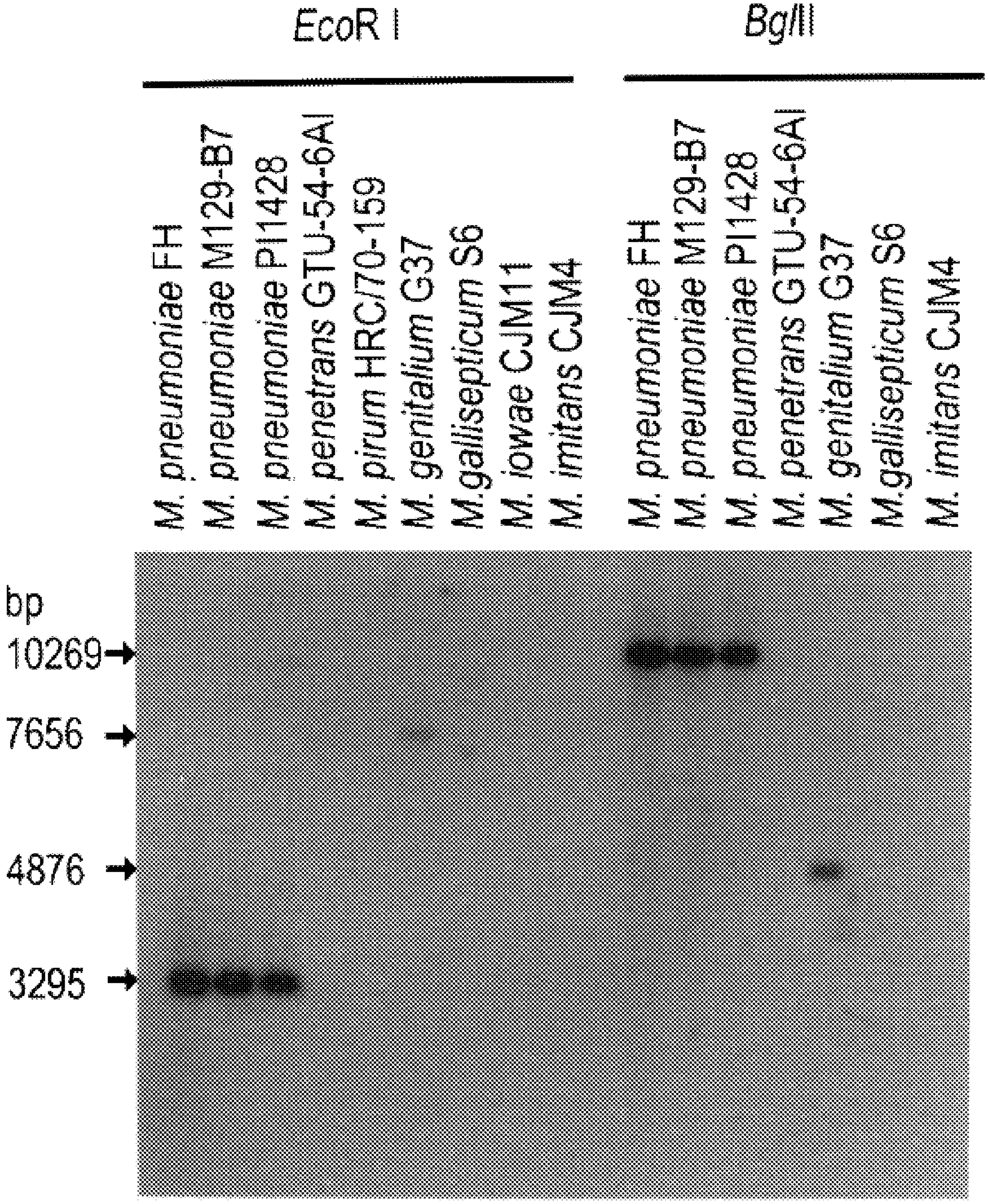

FIG. 7 is a photographic representation of a Southern blot showing the presence of homologues of the EcoRI fragment of *M. pneumoniae* in other species of Mycoplasma. Species names are indicated at the top of each lane. Fragment lengths (bp) are indicated on the left of the photograph. BglII and EcoRI designate restriction enzymes used to digest the genomic DNA samples derived from each species.

EXAMPLE 1
Strains

Reference herein to Mycoplasma shall be taken to refer to *M. pneumoniae* strain FH grown in SP4 medium in glass bottles at 37° C.

EXAMPLE 2
Triton X-114 partitioning of *M. pneumoniae* cellular proteins

Triton X-114 (Tx-114) partitioning adapted from the method of Bordier (1981) was used to isolate amphiphilic Mycoplasma proteins in the detergent phase. Triton X-114 was precondensed three times with PBS. The culture of *M. pneumoniae* in a volume of 700 ml was centrifuged to pellet the cells and the cell pellet washed twice with PBS. The cell pellet was resuspended in 5 ml ice cold 0.05% (v/v) Tx-114 in PBS, vortexed and incubated on ice for 60 minutes. This solution was then centrifuged at 11000×g at 4° C. for 35 min. The supernatant was layered on 1 ml ice cold 6% (w/v) sucrose, 0.06% (v/v) Tx-114 in PBS and incubated at 37° C. for 9 minutes followed by a low speed spin at 37° C. The supernatant containing water soluble proteins was aspirated to a separate tube and precipitated detergent resuspended in 2 ml cold PBS.

Figure 1:
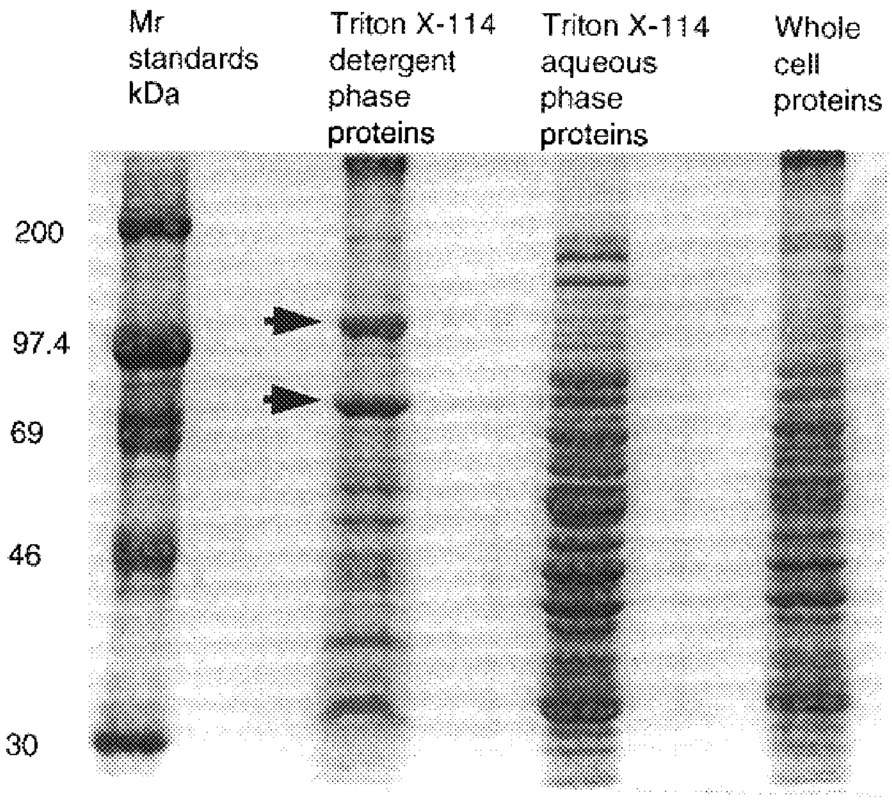

The detergent phase enriched from amphiphilic proteins was methanol-chloroform precipitated essentially according to Wessel and Flugge (1984). The dried protein pellet was resuspended in 4M urea PBS and examined by SDS PAGE of a 10% (w/v) polyacrylamide gel, followed by Coomassie blue staining of proteins contained therein. The most abundant *M. pneumoniae* amphiphilic protein was seen as bands at 110–116 kDa (FIG. 1).

EXAMPLE 3
Western blotting with sera from humans infected with *M. pneumoniae*

Figure 2:
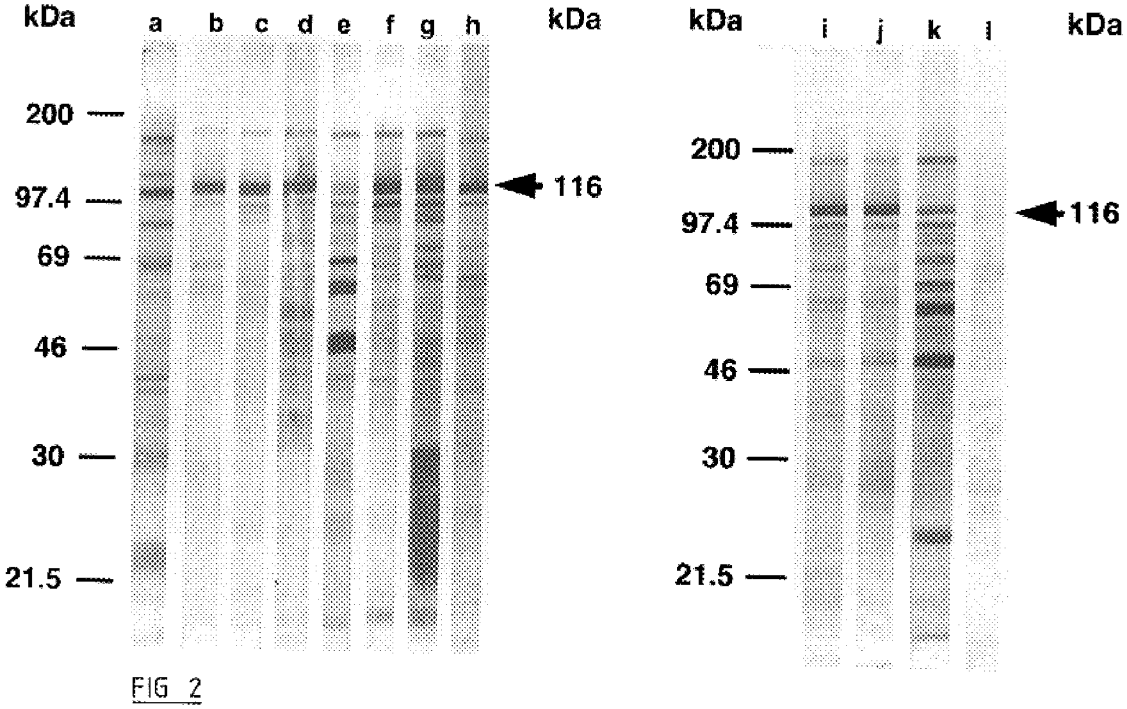
FIG. 2 is a photographic representation of a western blot of *M. pneumoniae* polypeptides probed with 10 different human sera (lanes a–l) obtained from patients infected with *M. pneumoniae*.

*M. pneumoniae* whole cell and amphiphilic protein preparations were separated by SDS PAGE, transferred to PVDF membrane and Western blotted by the method described by Jacobs et al (1986). A panel of ten human sera positive for anti *M. pneumoniae* IgG were used as probes. All the human sera reacted with the 116 kDa protein with 80% of the sera reacting with the 116 kDa protein as the most potent immunogen in the amphiphilic protein preparations. A human sera negative for anti *M. pneumoniae* did not bind any protein in the amphiphilic preparation (now shown). Whole cell *M. pneumoniae* preparations were probed with four human sera all of which reacted with the 116 kDa protein as the most potent immunogen (FIG. 2).

EXAMPLE 4
Immunisation of rabbits

*M. pneumoniae* amphiphilic protein preparations were electrophoresed on 10% (w/v) SDS polyacrylamide gels, the 110 kDa and 70 kDa bands were excised, fragmented by grinding between glass plates and used to immunise rabbits according to Harlow and Lane (1988). Twenty μg of protein was used per immunisation. The initial dose of antigen was delivered in Freunds complete adjuvant, subsequent doses were administered in Freunds incomplete adjuvant.

The resultant anti-110 kDa hyperimmune sera, hereinafter referred to as "rα110", was shown by western blotting to be reactive with the 110 kDa protein and to a far lesser extent with three other low molecular weight proteins, which may be proteolytic degradation products of same.

EXAMPLE 5
The *M. pneumoniae* 110 kDa polypeptide is a surface polypeptide

Figure 3:
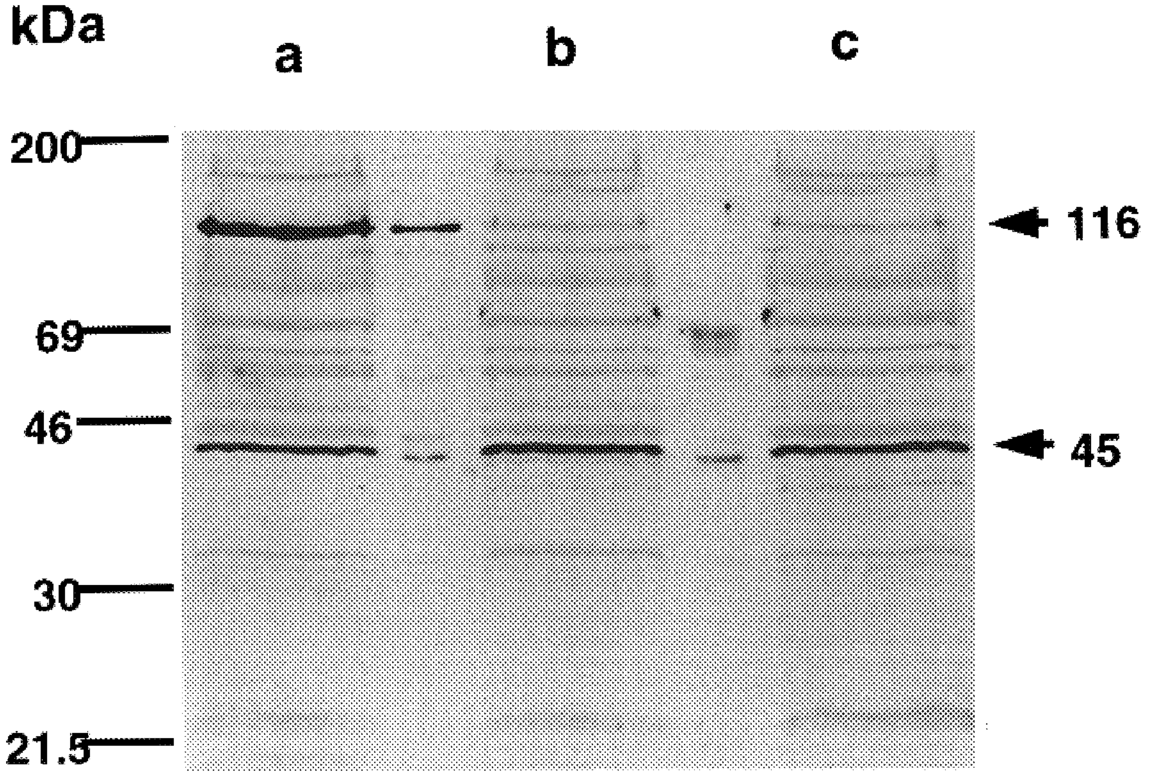
FIG. 3 is a photographic representation of a western blot of *M. pneumoniae* proteins, following trypsin-digestion of intact *M. pneumoniae*. The blot was probed with antisera raised against the 110 kDa polypeptide of *M. pneumoniae*.

Adherent *M. pneumoniae* from 50 ml of culture were rinsed 3 times with PBS, scraped into 20 ml PBS and divided into 8 ml aliquots. The washed cells were incubated at 37° C. with 600 μg trypsin for either 15 or 30 minutes, a control was incubated without trypsin for 30 minutes. Following the incubation, 400 $\mu$g of soyabean trypsin inhibitor was added to each tube. The tubes were centrifuged at 14,000×g, 4° C. for 30 minutes and the cell pellets washed, centrifuged again and resuspended in 50 $\mu$l PBS. Each suspension (25 $\mu$L) was examined by western blot analysis, probed with rα110. This analysis revealed the digestion of the 110 kDa polypeptide from the surface of intact cells in the presence of trypsin (FIG. 3). The 116 kDa polypeptide was digested further to yield a 45 kDa polypeptide when the incubation period was increased to 15 min or 30 min (FIG. 3).

EXAMPLE 6

DNA extraction

*M. pneumoniae* was grown in 700 ml SP4 medium in glass bottles. When the medium turned orange, the cells were harvested by scraping adherent cells into medium and centrifuging for 30' at 14,000 g, 4° C. The cell pellet was then washed twice with PBS. DNA was extracted from the cells according to Su et al (1988).

EXAMPLE 7

Sau3A I partial digest of *M. pneumoniae* DNA

*M. pneumoniae* DNA was digested with a series of dilutions of the restriction enzyme Sau3A I, essentially according to Sambrook et al (1989). The digested DNA was then examined by electrophoresis on a 1.2% (w/v) agarose gel. The dilution series determined that the optimal conditions for partial DNA digestion generating an average size fragment of 1500 bp was 0.035 U Sau3A I/1 ug DNA.

EXAMPLE 8

Removal of DNA fragments less than 100 bp by chromatography

Pharmacia MicroSpin Sephacryl S-400 HR columns were used to remove DNA fragments smaller than 100 bp from the Sau3A I partial-digested DNA preparation. Sau3A I digested *M. pneumoniae* DNA (10 $\mu$g DNA/50 $\mu$l sample volume) was applied to a column and fragments larger than 100 bp were eluted in sterile $dH_2O$.

The eluate was extracted with phenol:chloroform [1:1 (v/v)] and ethanol precipitated. The resulting DNA pellet was resuspended in 20 $\mu$l sterile $dH_2O$.

EXAMPLE 9

Preparation of cloning vector

Amrad vector pGEX-IN was employed for the expression cloning of *M. pneumoniae* Sau3A I digested DNA. In addition to an ampicillin resistance gene, the principal features of pGEX-IN are a lac $I^q$ mutant repressor (synthesised at 10× normal rate so that no expression of fusion protein occurs in absence of inducer), a tac promoter (hybrid trp-lac promoter), an ORF coding for the 26 kDa glutathione S-transferase from *Schistosoma japonicum* and a multiple cloning site (Smith and Johnson, 1988). This arrangement allows the expression of fusion proteins that may subsequently be purified by affinity interaction with Amrad Glutathione Sepharose 4B.

pGEX-IN DNA (10 $\mu$g) was digested with 40 Units of BamHI. The digested vector (6 $\mu$g) was treated with Bacterial Alkaline Phosphatase (BAP) obtained from GIBCO BRL and used according to the manufacturer's instructions, to remove 5' phosphates from same and thus prevent intramolecular ligation of the vector for occurring.

The BAP treated vector was extracted twice with phenol:chloroform [1:1(v/v)], ethanol precipitated and resuspended in sterile $dH_2O$ to a concentration of 27 ng/$\mu$l.

EXAMPLE 10

Ligation of *M. pneumoniae* Sau 3AI fragments to pGEX-1N vector DNA

Ligations were performed using T4 DNA ligase (Boehringer Mannheim) IU per ligation. Size-fractionated Sau3A I-digested *M. pneumoniae DNA* (0.5 $\mu$g) was ligated to 0.1 $\mu$g pGEX-1N, using standard procedures known in the art.

1/10 of the total ligation was used to transform electrocompetent *Escherichia coli* strain DH5α by electroporation using the BioRad Gene Pulser apparatus. Transformed bacteria were grown with shaking at 37° C. to facilitate expression of ampicillin resistance prior to spreading on LB plates containing 50 $\mu$g/ml ampicillin for overnight growth at 37° C.

EXAMPLE 11

Immunoscreen of expression library

Bacterial colonies were overlaid with Hybond C extra supported nitrocellulose membrane filters (Amersham). Filter lifts from plates were placed colony side up on fresh LB plates containing 100 $\mu$g/ml ampicillin and 2 mM IPTG and incubated at 37° C. for 3 hours to induce expression of fusion proteins. Cell lysis, and protein fixing were performed according to Sambrook et al (1989).

Bacterial colonies were overlaid with Hybond C extra supported nitrocellulose membrane filters (Amersham). Filter lifts from plates were placed colony side up on fresh LB plates containing 100 $\mu$g/ml ampicillin and 2 mM IPTG and incubated at 37° C. for 3 hours to induce expression of fusion proteins. Cell lysis, and protein fixing were performed according to Sambrook et al (1989).

Bacterial colonies were screened for expression of fusion protein, essentially according to Jacobs et al (1986), by probing with affinity-purified rα110 antisera. The rα110 antisera was affinity-purified by an adaption of the method of Beall and Mitchell (1986). Briefly, *M. pneumoniae* amphipilic protein preparations were transferred to PVDF membrane. The region of the membrane to which the 110 kDa protein had bound was excised, incubated with the antisera and washed. The antisera were then eluted with low pH glycine (i.e. 0.15M NaCl, 0.1M glycine pH 2.6) and neutralized immediately with 2M Tris/HCl pH 7.5. The eluted antisera did not cross-react with *E. coli* proteins, nor did it cross react with other *M. pneumoniae* proteins. Positive colonies were found at frequency of about 1/500.

Positive colonies were grown in SOC broth with 50 $\mu$g/ml ampicillin and subsequently plated out on LB plates with 50 $\mu$g/ml ampicillin. Single positive colonies were then patched onto duplicate gridded plates, one of which was then treated and screened with antisera as described previously. The resulting eleven positive clones were picked off the duplicate plate and grown in broth. Cultures were stored as glycerol stocks as described by Sambrook et al. (1989).

EXAMPLE 12

Characterisation of immuno-positive clones

DNA insert size was ascertained by digestion of CTAB plasmid minipreps with EcoRI and SmaI. Fusion protein expression was examined by SDS PAGE followed by western blotting of induced clones with rα110 antisera (FIG. 4). For this purpose, the anti *E. coli* specificity of rα110 was adsorbed to filter lifts of *E. coli* prior to use, as described by Sambrook et al (1989).

Immuno-positive clones were characterised further, by determining the size of the DNA inserts contained therein, and the size of internal EcoRI fragments (Table 3).

TABLE 3

Sizes of restriction enzyme digested *M. pneumoniae* genomic DNA fragments that hybridised to radiolabelled expression clones.

| Clone Number | Mr of expressed fusion protein (kDa) | *M. pneumoniae* DNA insert size (kbp) | Size of EcoR I fragments (kbp) |
|---|---|---|---|
| 1 | 74 | 2.9 | |
| 2 | 74 | 2.4 | |
| 11 | 74 | 3.6 | 0.22, 3.3 |
| 12 | 74 | 2.8 | |
| 3 | 51 | 0.7 | 0.14, 0.525 |
| 8 | 90 | 3.9 | 3.6, 0.6 |
| 9 | 49 | 2 | |
| 10 | 31 | 0.15 | |

EXAMPLE 13

Sequencing of expression clones

The clones listed in Table 3 were sequenced using Pharmacia$^{T7}$ Sequencing kit or Deaza G/A$^{T7}$ Sequencing Mixes as per instructions. Electrophoresis was performed with 5% (w/v) AT Biochem Long Ranger Gel in a Base Runner apparatus.

Analysis of sequence data suggested that clone 10 was the most 3' of the clones yet contained no stop codon. Clones 1, 2, 8, 9 and 12 shared identical sequence 3' to a Sau3AI site but 5' of this site had no homology indicating that ligation of Sau3AI digestion products had occurred prior to ligation with the vector. It was subsequently decided to clone the entire gene encoding the 110 kDa surface polypeptide, to facilitate sequencing of its 5' and 3' ends. Nucleotide sequence analysis showed that clone 8 was chimeric (i.e. containing genetic sequences from a gene unrelated to the 110 kDa polypeptide gene), since nucleotides 1–101 of clone 8 were identical to the *M. pneumoniae* His t-RNA gene.

EXAMPLE 14

Southern blots of *M. pneumoniae* genomic DNA probed with expression clones

DNA (150 ng) from clones 1, 3, 9, 10 and 11 was radiolabelled with 20 $\mu$Ci $\alpha^{32}$p-dCTP by random primed labelling (Boehringer Mannheim). Bgl II and EcoRI were used to digest 10 $\mu$g of genomic DNA from *M. pneumoniae, M. gallisepticum* strains Tsll and 6/85 and *M. synoviae* strains BC and 7NS. These digests were run on a 0.7% (w/v) agarose gel and transferred to nylon membrane (Amersham Hybond N$^{-}$) as per the manufacturers instructions. Digested genomic DNA from these Mycoplasma spp. was hybridised to each of the labelled clones as described by Sambrook et al. (1989) after the method of Southern (1971). Following hybridisation, membranes were then washed for 60 minutes 3 times in 0.1×SSC at 55° C.

As shown in Table 4, several *M. pneumoniae* genomic DNA fragments hybridised to the different clones. In contrast, clones from *M. pneumoniae* did not hybridize to DNA from *M. gallisepticum* or *M. synoviae.*

The 5' ends of clones 1 and 11 were suspected to be chimeric clones. This explanation accounts for the hybridisation of clone I to a Bgl II fragment other than the 10,269 bp Bgl II fragment, and also the hybridisation of clones 1 and 11 to EcoRI fragments other than the 7,874 bp and 3,295 bp EcoRI fragments. Alignment of homologous sequence from the different clones in conjunction with analysis of the Southern blot data allowed the construction of a map locating the expression clones on the gene for the 110 kDa protein and supported this conclusion.

TABLE 4

Sizes of restriction enzyme digested *M. pneumoniae* genomic DNA fragments that hybridised to radiolabelled expression clones.

| Clone | Size of hybridizing Bgl II fragments (bp) | Size of hybridizing EcoR I fragments (bp) |
|---|---|---|
| #1 | 10,269 | 20,647 |
| | 9,124 | 7,874 |
| | | 3,295 |
| #3 | 10,269 | 7,874 |
| | | 3,295 |
| #9 | 10,269 | 3,295 |
| #10 | 10,269 | 7,874 |
| #11 | 10,269 | 7,874 |
| | | 3,295 |
| | | 2,464 |

EXAMPLE 15

Cloning of *M. pneumoniae* EcoRI fragments of the 110 kDa surface polypeptide gene I) Synthesis of probe Analysis of the 1325 bp sequence obtained from clone 8 revealed an Nhe I restriction site at nucleotide 244 unique not only for this sequence but also for the 850 bp of non-contiguous clones 3 and 10. pGEX-1N does not contain an Nhe I site so digestion of expression clone 8 with Sma I (unique for pGEX-1N and 3' to BamHI in the multi cloning site) and the Nhe I excised a 3062 bp fragment of the *M. pneumoniae* DNA insert.

The 3062 bp fragment was excised from an agarose gel and purified with Prepagene (BioRad). The fragment (36 ng) was radioactively labelled as described in the preceding Examples.

The radiolabelled probe was hybridised to one of the Southern blots described previously. Consistent with data presented in Table 4, the 3062 bp probe hybridized to EcoRI fragments of 7,874 bp and 3,295 bp and to a single Bgl II fragment of 10,269 bp in *M. pneumoniae* DNA. Thus, the probe was specific for the 110 kDa protein gene and was suitable for use in screening libraries to obtain additional clones.

II Construction of Library

*M. pneumoniae* genomic DNA (10 $\mu$g) was digested with 50 U EcoRI, and applied to a Pharmacia MicroSpin Sephacryl S-400 HR volume in a total volume of 50 $\mu$l, to remove fragments smaller than 100 bp. The eluted DNA was extracted with phenol:chloroform [1:1 (v/v)], ethanol precipitated and resuspended in sterile $dH_2O$.

Plasmid pUCBM20 (Boehringer Mannheim) was cut with EcoRI and treated with Bacterial Alkaline Phosphatase followed by two extractions using phenol:chloroform [1:1 (v/v)], ethanol precipitation and resuspension in sterile $dH_2O$.

The EcoRI digested, 5' dephosphorylated pUCBM20 was ligated to EcoRI digested *M. pneumoniae* DNA at a vector:insert ration of 1:3, in a total volume of 9 $\mu$l.

Electrocompetent *E. coli* strain DH5$\alpha$ were transformed with 1 $\mu$l of the ligation reaction and plates as for the pGEX-1N cloning.

The plates were overlaid with Hybond N (Amersham) filters and filters subsequently prepared for hybridisation according to the manufacturers instructions. Screening of the library with radiolabelled DNA probe was as described by Sambrook et al (1989).

Positive colonies were selected and streaked on LB plates with 50 μg/ml ampicillin. Following overnight growth individual colonies were picked, patched onto gridded LB plates with ampicillin and grown overnight. Filter lifts were taken of the patched clones and screened as previously. Positive clones were picked and grown in SOC broth with ampicillin overnight for CTAB plasmid miniprep analysis.

Agarose gel electrophoresis of EcoRI digested miniprep DNA samples from the positive clones allowed identification of clones containing either the 7,874 bp or 3,295 bp EcoRI fragments spanning the *M. pneumoniae* 110 kDa protein gene.

These clones were subsequently shown to contain DNA sequence beyond the 5' and 3' limits of the clones isolated from the Sau3AI *M. pneumoniae* pGEX-1N expressions library.

EXAMPLE 16

Sequence analysis of the 16 kDa and 116 kDa proteins

Ribosomal binding site (RBS) or promoter could be identified for the ORF encoding the 116 kDa protein. However, the ORF encoding the 16 kDa protein was preceded by a consensus Shine-Dalgarno sequence (AGGAGGU) commencing at nucleotide position 239 of SEQ ID NO: 3. These data suggest that the linked ORF's encoding the 16 kDa and 116 kDa proteins are part of the same operon.

Analysis of the derived amino acid sequence of the 16 kDa polypeptide of *M. pneumoniae* revealed a consensus for a prokaryotic prolipoprotein signal sequence cleaved by signal peptidase II: FASLSFKLIEC with the cysteine at amino acid position 31 of SEQ ID NO: 1 (FIG. 5). The PSORT program, predicted the 16 kDa protein to be a bacterial membrane protein.

EXAMPLE 17

The NH2 terminal half of the 116 kDa protein is highly antigenic

The translation of the ORF coding for the 116 kDa protein (SEQ ID NO:2) indicated a hydrophobic peak for the amino terminal 26 amino acids with a mean Kyte Doolittle hydrophobicity value of 162. This value was markedly higher than those for the penultimate hydrophobic peak, 75 and the entire 116 kDa protein, −31. As no consensus signal peptidase cleavage site could be detected following the leader sequence, it is probable that this region of relatively high hydrophobicity is involved in membrane association.

EXAMPLE 18

Production of derivatives of the 116 kDa polypeptide

GST fusion proteins were prepared comprising various regions derived from the 116 dDa *M. pneumoniae* polypeptide. Fusion proteins were produced by subcloning Sau3A1 fragments of the open reading frame encoding the 116 kDa polypeptide into the pGEX expression vector, to produce an in-frame fusion with the GST-encoding region of the vector (FIG. 5). Positions of fusion proteins within the 116 kDa *M. pneumoniae* polypeptide are indicated in Table 5.

Antisera were prepared against the GST fusion proteins using standard procedures.

EXAMPLE 19

Ability of antisera against fusion proteins to detect *M. pneumoniae*

Thirty four serum samples from patients with suspected *M. pneumoniae* infection were assessed for anti *M. pneumoniae* antibodies by the Serodiamycoll particle agglutination assay; 33 were positive. These sera were used at a dilution of 1/600 in Western blot to assess 1 gG reactivity with 5 purified GST fusion proteins derived from the 116 kDa protein. Results are presented in Table 6. The fusion protein 661, containing the uncleaved signal sequence, reacted with 29 of the 34 sera (85%). Fusion protein 10C reacted with 13 sera and fusion protein 10C and fusion protein FP3. Only one serum unreactive with fusion protein 661 reacted with another fusion protein, FP3. One serum was reactive with the GST negative control (2.9%).

TABLE 5

Position of fusion proteins within the 116 kDa polypeptide of *M. pneumoniae*

| Fusion protein | Nucleotide position | Amino acids (SEQ ID No:2) |
|---|---|---|
| 661 | 25–1422 | 9–473 |
| 3C | 1399–2127 | 467–709 |
| FP2 | 2125–2550 | 709–850 |
| 10C | 2536–2689 | 846–896 |
| FP3 | 2659–2886 | 887–962 |
| FP4 | 2451–3087 | 969–1029 |

The reactivity of fusion protein 661 with sera from humans infected with *M. pneumoniae* suggests potential in serodiagnosis. Other serum samples will be assessed by the more sensitive technique of ELISA.

EXAMPLE 20

Other closely related mycoplasma lack homologous genes

The possibility of ORF's homologous to the *M. pneumoniae* 16 kDa and 116 kDa ORF's in the species of the *M. pneumoniae* group and the phylogenetically closely related *M. penetrans* and *M. iowae* was investigated by Southern blots, only *M. pneumoniae* and *M. genitalium* DNA hybridised to the probes.

TABLE 6

Detection of *M. pneumoniae* in patient samples using various antisera

| Recombinant Vector | Fusion Protein | Sera from infected patients positive for IgG |
|---|---|---|
| pGEX 3XMPFP3 | FP3 | 32 |
| pGEX 1NMP10 | 10C | 38 |
| pGEX 3XMPFP2 | FP2 | 18 |
| pGEX 1NMP3 | 3C | 24 |
| pGEX 3XMP661 | 661 | 85 |

Whole cell proteins were analysed by Western blot for antigenic cross reactivity with the 116 kDa protein of *M. pneumoniae*. Only proteins derived from *M. pneumoniae* reacted with the monospecific rabbit anti 116 kDa. The entigenicity and specificity of the 116 kDa protein warrant further investigation of its potential as a specific and sensitive serodiagnostic reagent.

EXAMPLE 21

Isolation of a homologue of the 16 kDa—encoding and 116 kDa—encoding open reading frames The genomic sequence of *M. genitalium* Fraser et al. (1995) contains contiguous open reading frames corresponding to the 16 kDa (MG074) and 116 kDa (MG075) reading frames of *M. pneumoniae*. The *M. genitalium* ORF MG074 has 58.4% nucleotide identity and 37.3% amino acid identity to the gene for the 16 kDa protein. The *M.*

*genitalium* ORF MG075 has 61% nucleotide identity and 52% amino acid identity to the gene for the 116 kDa protein of *M. pneumoniae*. Neither of the *M. genitalium* ORF's have been assigned a function although on the basis of this work they can be described as surface proteins.

MG074 and MG075 are adjacent, in the same order and on the same strand of the chromosome as the ORF's encoding the 16 kDa and 116 kDa proteins.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES

1. Ausubel, F. M. et al. (1987) In: Current Protocols in Molecular Biology, Wiley Interscience (ISBN 047140338).
2. Beall, J. A., and G. F. Mitchell 1986. *J. Immunol. Methods.* 86:217–223.
3. Bordier, C. 1981. *J. Biol. Chem.* 257:1604–1607.
4. Cimolai, N. et al. 1989. *J. Rheumatol.* 16:1150–2.
5. Cimolai, N., et al. 1992. *Microbiol Immunol.* 36:465–78.
6. Cole et al. (1985) In Monoclonal antibodies in cancer therapy, Alan R. Bliss Inc., pp 77–96;
7. Crossway et al. (1986) *Mol. Gen. Genet.* 202: 179–185;
8. Fraser, C. M., et al *Science.* 270: 397–403.
9. Fromm et al. (1985) *Proc. Natl. Acad. Sci.* (*USA*) 82:5824–5828;
10. Goodman et al. (1987) Ti Biopolymers 26: 525–532;
11. Granstrom, M., T. et al *J Med Microbiol.* 40:288–92.
12. Harlow, E., and D. Lane (1988). In: Antibodies a Laboratory Manual, Cold Spring Harbor Laboratory.
13. Huse et al. (1989) *Science* 246: 1275–1281;
14. Jacobs, E., et al 1986). *Journal of Clinical Microbiology.* 23:517–522.
15. Koskiniemi, M (1993). CNA manifestations associated with *Mycoplasma pneumoniae* infections: summary of cases at the University of Helsinki and review. *Clin Infect Dis.*
16. Kohler and Milstein (1975) *Nature,* 256: 495–499;
17. Kozbor et al. (1983) *Immunol. Today* 4: 72;
18. Mierke et al. (1990) *Int. J. Peptide Protein Research,* 35:35–45;
19. Paszkowski et al. (1984) *EMBO J.* 3:2717–2722;
20. Portoghese et al. (1990) *J. Med. Chem.* 33:1714–1720;
21. Sambrook, J., E. F. Fritsch, and T. Maniatis 1989. Molecular Cloning: A Laboratory Manual, second. Cold Spring Harbor Laboratory Press.
22. Smith, D. B., and K. S. Johnson 1988. *Gene.* 67:31–40.
23. Southern, E. M. 1975. *Journal of Molecular Biology.* 98:503.
24. Su, C. J., et al 1988. *Infect Immun.* 56:3157–61.
25. Wessel, D., and U. I. Flugge 1984. *Analytical Biochemistry.* 138:141–143.
26. Yayoshi, M., et al 1992. *Microbiol Immunol.* 36:455–64.
27. Zagami, A. S. et al, Detection of *Mycoplasma pneumoniae* in CSF of a patient with encephalitis. In: Australia Society for Microbiology Annual Scientific Meeting, 1994, Melbourne, Victoria, Australia: Australian Society for Microbiology.

What is claimed is:

1. An isolated or recombinant immunogenic polypeptide of a Mycoplasma ssp. having a molecular weight selected from the group consisting of: (i) a predicted molecular weight as determined from the amino acid sequence of said polypeptide of approximately 16 kDa or 116 kDa; and (ii) a molecular weight of 110 kDa as determined using SDS/PAGE and wherein said polypeptide comprises an amino acid sequence selected from the group consisting of:

(i) the amino acid sequence set forth in SEQ ID NO:1;

(ii) the amino acid sequence set forth in SEQ ID NO:2;

(iii) the amino acid sequence set forth in SEQ ID NO:4;

(iv) the amino acid sequence set forth in SEQ ID NO:5;

(v) an amino acid sequence having at least 70% sequence identity to any one of (i) to (iv), wherein said polypeptide is immunogenic; and (vi) an immunogenic fragment of any one of (i) to (iv).

2. The isolated or recombinant immunogenic polypeptide according to claim 1 wherein said polypeptide is isolated from *Mycoplasma pneumoniae* or wherein said polypeptide is isolated from a recombinant bacterial cell expressing said polypeptide.

3. The isolated or recombinant immunogenic polypeptide according to claim 2 wherein said polypeptide is a surface polypeptide which has adhesion properties.

4. The isolated or recombinant immunogenic polypeptide according to claim 1 wherein the polypeptide has an amino acid of an immunogenic fragment comprising an amino acid sequence selected from the group consisting of:

(i) amino acid residues 9 to 473 of SEQ ID NO:2;

(ii) amino acid residues 467–709 of SEQ ID NO:2;

(iii) amino acid residues 709 to 850 of SEQ ID NO:2;

(iv) amino acid residues 846 to 896 of SEQ ID NO:2;

(v) amino acid residues 887 to 962 of SEQ ID NO:2; and (vi) amino acid residues 969 to 1029 of SEQ ID NO:2.

5. The isolated or recombinant immunogenic polypeptide according to claim 4 wherein the polypeptide has an amino acid sequence of an immunogenic fragment comprising an amino acid residues 9 to 473 of SEQ ID NO:2 or a fragment thereof comprising a B or T cell epitope.

6. The isolated or recombinant immunogenic polypeptide according to claim 1 wherein said polypeptide is encoded by an isolated DNA molecule selected from the group consisting of:

(i) a DNA molecule comprising a sequence of nucleotides of SEQ ID NO:3;

(ii) a DNA molecule comprising a nucleotide sequence having at least 70% identity to SEQ ID NO:3;

(iii) a DNA molecule comprising a nucleotide sequence that is capable of hybridizing to SEQ ID NO:3; and (iv) a fragment of (i) that encodes an immunogenic fragment of said immunogenic polypeptide.

7. The isolated or recombinant immunogenic polypeptide according to claim 1 derived from Mycoplasma ssp. selected from the group consisting of *M. penetrans, M. iowae, M. gallisepticum, M. genitalium, M. imitans, M. muris, M. urealyticum* and *M. pirum.*

8. The isolated or recombinant immunogenic polypeptide according to claim 7 derived from *M. genitalium.*

9. The isolated or recombinant immunogenic polypeptide according to claim 1 wherein said polypeptide is a surface polypeptide.

10. The isolated or recombinant immunogenic polypeptide according to claim 1 when expressed in a virus particle, prokaryotic cell or eukaryotic cell.

11. The isolated or recombinant immunogenic polypeptide according to claim 10 wherein the prokaryotic cell is a bacterial cell.

12. The isolated or recombinant immunogenic polypeptide according to claim 11 wherein the bacterial cell is an *Escherichia coli* cell or a Mycoplasma ssp. cell.

13. The isolated or recombinant immunogenic polypeptide according to claim 10 wherein said polypeptide is expressed as a fusion polypeptide.

14. The isolated or recombinant immunogenic polypeptide according to claim 13 wherein the fusion polypeptide is a fusion with glutathione-s-transferase.

15. A vaccine composition for the therapeutic or prophylactic treatment of a mammalian subject against infection by a Mycoplasma ssp., said composition comprising the isolated or recombinant immunogenic polypeptide according to claim 1 in an amount sufficient to mediate an immune response when administered to said mammal and a pharmaceutically acceptable carrier or diluent.

16. The vaccine composition according to claim 15 wherein the mammal is a human.

17. The vaccine composition according to claim 15 wherein the means of administration is injection or ingestion.

18. The vaccine composition according to claim 15 wherein the Mycoplasma ssp. is *M. pneumoniae.*

19. The vaccine composition according to claim 15 wherein said vaccine composition is capable of inducing humoral immunity against said Mycoplasma ssp.

20. The vaccine composition according to claim 19 wherein said vaccine composition further prevents the onset, development or progression of symptoms associated with *M. pneumoniae* infection with administered to said mammal.

21. The vaccine composition according to claim 20 wherein the symptoms associated with *M. pneumoniae* infection are selected from the list comprising atypical pneumoniae, lung lesions and inflammatory reactions of the respiratory tract or central nervous system.

22. The vaccine composition according to claim 15 further comprising an adjuvant.

23. An isolated nucleic acid molecule wherein said nucleic acid molecule encodes an isolated or recombinant immunogenic polypeptide which comprises an amino acid sequence having at least 70% identity to any of SEQ ID NOs:1, 2, 4 or 5.

24. A genetic construct comprising the isolated nucleic acid molecule according to claim 23 operably linked to a promoter sequence which is capable of regulating expression of said nucleic acid molecule in a virus particle, prokaryotic cell or eukaryotic cell.

25. The genetic construct according to claim 24 when used to produce a recombinant polypeptide which comprises an amino acid sequence having at least 70% identity to any one of SEQ ID NOs:1, 2, 4 or 5.

26. The genetic construct according to claim 25 wherein the recombinant polypeptide is a polypeptide immunogen.

27. An isolated or recombinant immunogenic polypeptide of Mycoplasma ssp. having a molecular weight selected from the group consisting of: (i) a predicted molecular weight as determined from the amino acid sequence of said polypeptide of approximately 16 kDa or 116 kDa; and (ii) a molecular weight of 110 kDa as determined using SDS/PAGE wherein said isolated or recombinant polypeptide is detected by a process comprising:

(i) hybridizing nucleic acid of Mycoplasma spp. to a probe or primer comprising the nucleotide sequence set forth in SEQ ID NO:3 under at least low stringency hybridization conditions and isolating the hybridized nucleic acid;

(ii) expressing the hybridized nucleic acid in a cell, tissue, organ or organism for a time and under conditions sufficient for transcription and translation of said nucleic acid to occur; and (iii) detecting the expressed protein.

28. An isolated or recombinant immunogenic polypeptide of Mycoplasma ssp. having a molecular weight selected from the group consisting of: (i) a predicted molecular weight as determined from the amino acid sequence of said polypeptide of approximately 16 kDa or 116 kDa; and (ii) a molecular weight of 110 kDa as determined using SDS/PAGE wherein said isolated or recombinant polypeptide is detected by a process comprising contacting protein of said Mycoplasma with an antibody molecule that binds specifically to the isolated or recombinant protein of claim 1.

* * * * *

UNITED STATES PATENT AND TRADEMARK OFFICE

CERTIFICATE OF CORRECTION

PATENT NO. : 6,171,589

DATED : January 9, 2001

INVENTOR(S) : Browning et al.

It is certified that error appears in the above-identified patent and that said Letters Patent is hereby corrected as shown below:

column 21, line 61, replace "reacted" with --unreacted--.

column 30, line 40 replace "now shown" with --not shown--.

column 36, line 18 replace "1 gG" with --IgG--.

column 36, line 55 replace "entigenicity" with --antigenicity--.

Signed and Sealed this

Twenty-second Day of May, 2001

*Attest:*

Nicholas P. Godici

NICHOLAS P. GODICI

*Attesting Officer*

*Acting Director of the United States Patent and Trademark Office*